(12) United States Patent
Maruo

(10) Patent No.: US 6,292,583 B1
(45) Date of Patent: Sep. 18, 2001

(54) IMAGE INFORMATION PROCESSING APPARATUS

(75) Inventor: Kazuyuki Maruo, Sendai (JP)

(73) Assignee: Advantest Corporation, Tokyo (JP)

( * ) Notice: Subject to any disclaimer, the term of this patent is extended or adjusted under 35 U.S.C. 154(b) by 0 days.

(21) Appl. No.: 09/163,809

(22) Filed: Sep. 30, 1998

(30) Foreign Application Priority Data

Sep. 30, 1997 (JP) .................................................... 9-283092

(51) Int. Cl.[7] ....................................................... G06K 9/36
(52) U.S. Cl. ........................... 382/149; 348/126; 382/248; 382/281
(58) Field of Search .................................... 382/276, 281, 382/282, 288, 291, 199, 248, 147, 149, 151, 145, 141; 348/86, 126

(56) References Cited

U.S. PATENT DOCUMENTS

| | | | |
|---|---|---|---|
| 4,868,752 | * | 9/1989 | Fujii et al. ...................... 364/424.02 |
| 5,418,892 | * | 5/1995 | Aghajan et al. ...................... 395/118 |
| 5,576,548 | * | 11/1996 | Clarke et al. ......................... 250/369 |
| 5,616,905 | * | 4/1997 | Sugiyama ............................. 235/456 |
| 5,740,268 | * | 4/1998 | Nishikawa et al. .................. 382/132 |

* cited by examiner

Primary Examiner—Joseph Mancuso
Assistant Examiner—Yosef Kassa
(74) Attorney, Agent, or Firm—David N. Lathrop; Gallagher & Lathrop

(57) ABSTRACT

There is provided an image information processing apparatus capable of detecting a defect on a device even from an unclear SEM image thereof, and without using a golden device or a CAD data, at high speed. A two dimensional Wavelet transform is applied to an input digital image data. A threshold value process (a binarization process) is then applied to longitudinal line detection components and lateral line detection components obtained by the two dimensional Wavelet transform to create respective binarization images of the longitudinal line detection components and the lateral line detection components. A Hough transform is applied to each binarization image to obtain a position and a size of an object to be detected. If a threshold value process is applied to an image in a parameter space obtained by the Hough transform, a detection of particular figure information becomes easy. With respect to the binarization image, active pixels are grouped such that the same label is given to adjacent active pixels. A position and a size of an object to be detected can automatically be specified by finding center of gravity coordinates of each of the labels.

36 Claims, 27 Drawing Sheets

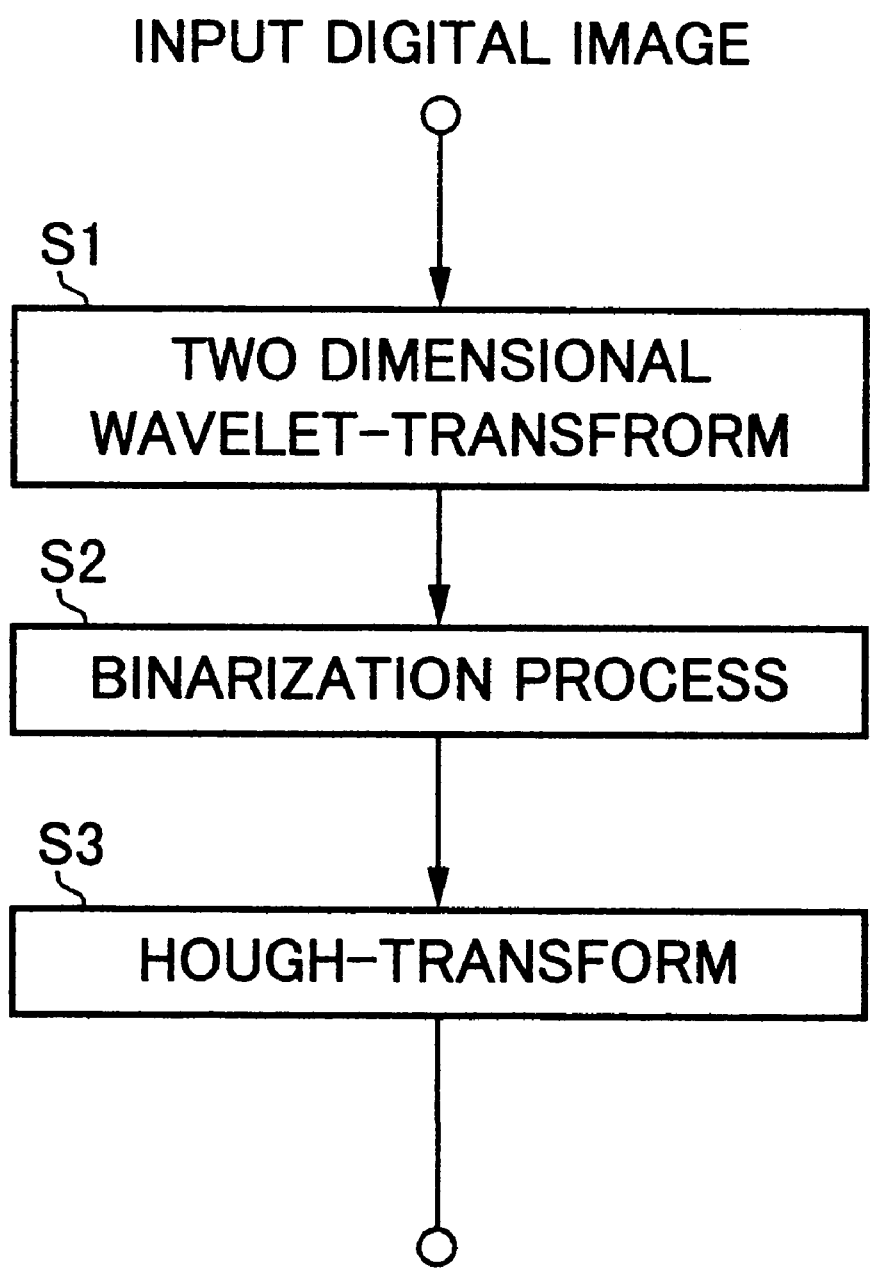

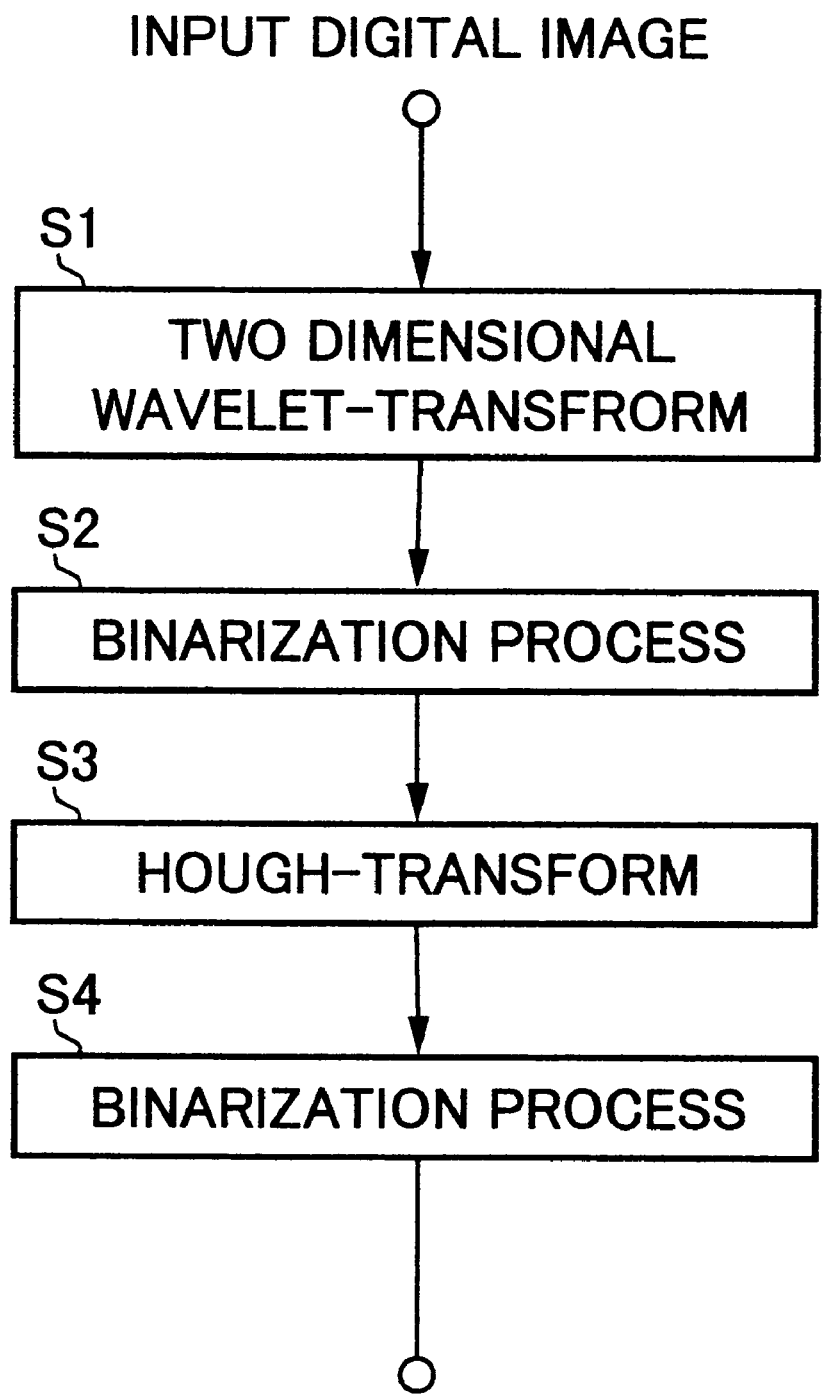

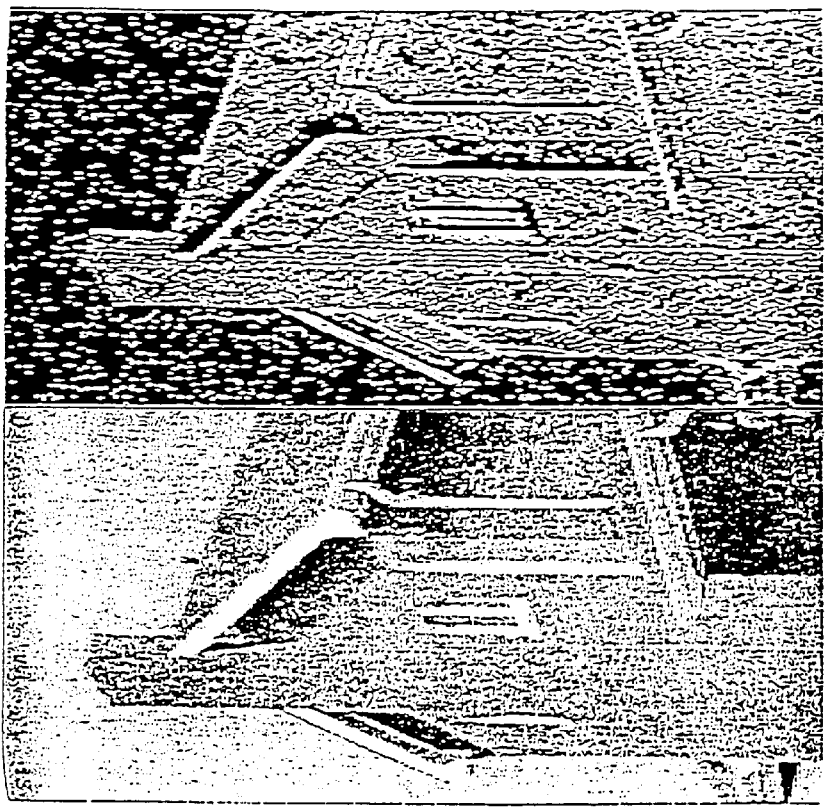
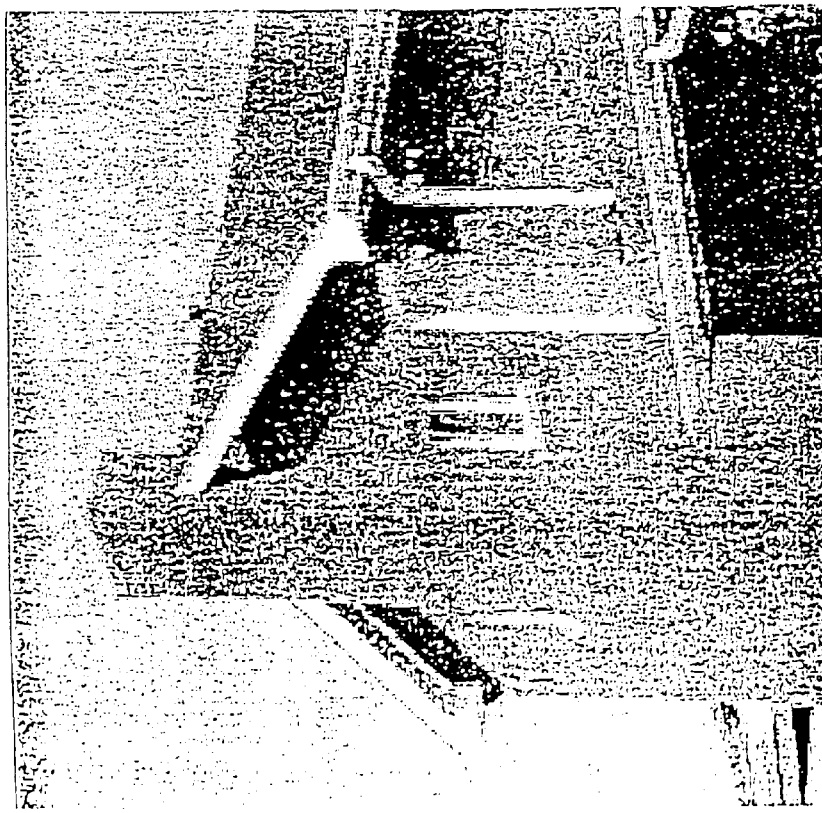
FIG.5A
FIG.5B

IMAGE INFORMATION PROCESSING APPARATUS

BACKGROUND OF THE INVENTION

1. Field of the Invention

The present invention relates to an apparatus for recognizing and detecting defect information such as an alien or foreign substance or substances occurring on a semiconductor wafer, a printed board or the like. Herein, the term "printed board" is intended to refer generically to a single-sided, a double-sided and a multi-layer printed boards inclusive of flexible printed circuits.

2. Description of the Related Art

A defect occurring on or a foreign substance (or material) mixing in a printed board or a semiconductor wafer during manufacturing process thereof causes a defective or faulty product. Therefore, it is necessary to rapidly detect any defect or foreign substance at the time when it has occurred on or mixed in the printed board or the semiconductor wafer.

There have been conventionally proposed image information processing apparatus each of which detects, recognizes or judges a defect or an alien substance as mentioned above on the basis of a photograph of a printed board, or an image or picture of a semiconductor wafer obtained by having taken it using an optical microscope or the like to input it to the apparatus. Almost all of the procedures of these image information processing apparatus are based on digital image processing in which an image is digitally treated or processed, and they perform the image processing using a computer.

Heretofore, as the defect detecting procedure using the image processing, the following have been mainly known:

(a) golden device comparison method;
(b) CAD (computer-aided design) data comparison method;
(c) die to die comparison method; and
(d) FFT method.

In the golden device comparison method (a), an image of an ideal semiconductor wafer having no defect (hereinafter referred to as golden device) is previously provided. An image of an object (wafer or printed board) to be inspected is compared with the image of the golden device to detect a defect of the object. The comparison between two images means a processing in which values of picture elements or pixels of the one image are taken from values of picture elements or pixels of the other image for their corresponding picture elements one by one to create a difference image with respect to picture element values between the two images. In case the image of the object to be inspected has no defect, the two images being compared are all the same, and the resulting difference image will be a flat image having its all picture element values of 0 throughout the entire image. However, in case the image of the object to be inspected has a defect or foreign substance, picture elements having values other than 0 appear concentratedly in that region where the image of the object has a defect or foreign substance. In this instance, therefore, the defect or the foreign substance can be detected by extracting a group of the picture elements each having a value other than 0 to obtain the size and/or the center of the gravity (centroid).

In the CAD data comparison method (b), image data of a manufactured wafer is compared with CAD image data which is data information of the device to be inspected designed by the CAD. On the basis of this comparison process, a defect or an alien substance on the device to be inspected can be detected similarly to the above-mentioned golden device comparison method (a).

In the die to die comparison method (c), the fact is utilized that a plurality of identical chips (hereinafter referred to as dies) are arrayed or disposed on a single wafer, and image data of adjacent dies are compared with each other. On the basis of this comparison process, a defect or a foreign substance on the device to be inspected can be detected similarly to the above-mentioned golden device comparison method (a) and the CAD data comparison method (b).

In the FFT method, the features are utilized that a defect on a wafer locally occurs, whereas a wiring pattern or printed circuit pattern thereon is periodic, and a defect on a wafer to be inspected is detected by removing a wiring pattern or printed circuit pattern thereon. That is, a defect on the wafer to be inspected can be detected by Fourier-transforming an input wafer pattern image by application of a two dimensional FFT (Fast Fourier-Transform) or the like thereto, removing a specific space frequency component corresponding to a wiring pattern or printed circuit pattern in a space frequency region by utilization of a band stop filler or the like, and thereafter, applying an inverse FFT thereto.

In the case that the above-mentioned golden device comparison method (a) is utilized, a golden device image must be provided in advance. In order to create a golden device image, a sample having no defect must be found out first. The operation for finding out the sample having no defect must carefully be performed by human eyes. In addition, in view of a recent tendency of "various kinds of products and a small amount of production of each", there are provided various kinds of semiconductor wafer patterns and many changes in pattern design are effected. A golden device image must be created for each of all of those varieties and/or design changes. This requires a considerable labor or work load.

The above-mentioned CAD data comparison method (b) is efficient because it is not necessary to look for a golden device by human eyes like the above-mentioned item (a). Incidentally, in recent years, a high-density integration of a semiconductor chip has been in progress and hence, a conventional optical microscope cannot be used for acquiring a detailed image of a wafer pattern. For this end, a scanning electron microscope (SEM) or the like has been in use. A SEM image contains therein more noise as compared. to an optical microscope image. Therefore, when a differential image is created between CAD data having no noise and a SEM image, a disadvantage is caused that many noises other than defects are detected.

Furthermore, the methods of the above-mentioned items (a) and (b) both require a precise registration or positioning of the two images at the first time upon performing the comparison between both images.

In the above-mentioned die to die comparison method (c), no registration or positioning of two dies (images) is basically required because adjacent dies are compared with each other. However, there is a drawback in this method that if the two dies should have similar defects at the same positions thereof by accident, those defects cannot be detected. In addition, similarly to the above-mentioned item (b), noises other than defects are detected if the comparison is applied to a SEM image.

In the above-mentioned FFT method (d), it is possible to detect a defect on a device even though a SEM image thereof was used for comparison. However, this method requires a very long processing time. For example, when a two dimensional Fourier-transform is applied to a digital image comprised of 512×512 pixels, approximately $1.31 \times 10^8$ additions/subtractions and $8.39 \times 10^8$ multiplications are required. In addition, a complicated wiring or printed circuit pattern of an MPU or the like cannot be correctly removed by a filtering process in a space frequency region.

SUMMARY OF THE INVENTION

It is a first object of the present invention to provide an image information processing apparatus which can detect a defect on a device even from an unclear SEM image thereof from which a defect on the device cannot be correctly detected by use of the image comparison methods of the above-mentioned items (a), (b) and (c) because of a strong influence of noise.

It is a second object of the present invention to provide an image information processing apparatus which can detect a defect on a device from an independent image thereof to be inspected without using a golden device or a CAD data required in the image comparison methods of the above-mentioned items (a) and (b).

It is a third object of the present invention to provide an image information processing apparatus which can detect a defect on a device at high speed from an image thereof to be inspected without spending a prodigious amounts of processing time, unlike the FFT method of the above-mentioned item (d).

In order to accomplish the above-mentioned objects, in accordance with a first aspect of the present invention, there is provided an image information processing apparatus for inspecting, recognizing or judging an object using its image comprising: two dimensional Wavelet transform means for applying a two dimensional Wavelet transform to an input digital image; binarization processing means for applying a threshold value process to longitudinal line detection components and lateral line detection components obtained by the application of the two dimensional Wavelet transform to the input digital image data to create a binarization image of the longitudinal line detection components and a binarization image of the lateral line detection components; and Hough transform means for applying a Hough transform to the binarization images obtained by the binarization processing means to find a position and a size of an object to be detected.

The image information processing apparatus may further comprise second binarization processing means for applying a threshold value process to the images in a parameter space obtained by the Hough transform means to detect specific figure information.

In addition to the second binarization processing means, the image information processing apparatus may further comprise labeling processing means for labeling adjacent active images in the binarization images in a parameter space with the same label to group them, the binarization images being obtained by applying a binarization process to the result of the Hough transform process, and center of gravity calculating means for finding center of gravity coordinates for each of the labels obtained by the labeling process.

The image information processing apparatus may further comprise noise removing means for applying a localized noise removal operation to the input digital image.

In addition to the noise removing means, the image information processing apparatus may further comprise isolated point removing means for removing an isolated active image from the binarization images of the longitudinal line detection components and the lateral line detection components obtained by applying the binarization process to the result of the two dimensional Wavelet transform process.

In a preferred embodiment, the binarization processing means for applying a binarization process to the result of the two dimensional Wavelet transform process is an absolute value binarization processing means for applying a threshold value process to the absolute value of the result of the two dimensional Wavelet transform process.

The Hough transform means may be Hough transform means for especially detecting x and y coordinates of a center of a circle and a radius of the circle.

The Hough transform means may be means for Hough transforming into the same parameter space the two binarization images respectively corresponding to the longitudinal line detection components and the lateral line detection components obtained by the two dimensional Wavelet transform process.

The Hough transform means may be Hough transform means for either one of the two binarization images respectively corresponding to the longitudinal line detection components and the lateral line detection components obtained by the two dimensional Wavelet transform process.

The image information processing apparatus may further comprise energy calculating means for calculating energy of each of the longitudinal line detection components and the lateral line detection components obtained by the two dimensional Wavelet transform process, and the Hough transform means Hough transforms to the binarization image corresponding to the components having lower energy.

In a preferred embodiment, the binarization threshold value of the second binarization processing means for the parameter space by the Hough transform for a circle is a threshold value changing in accordance with the magnitude of a radius parameter.

The image information processing apparatus may further comprise overlap detection removing means for removing, when a plurality of objects to be detected overlap in terms of their positions, the overlapping object or objects.

BRIEF DESCRIPTION OF THE DRAWINGS

FIG. 1A is a flow chart for explaining a first basic operation of the image information processing apparatus according to the present invention;

FIG. 1B is a flow chart for explaining a second basic operation of the image information processing apparatus according to the present invention;

FIG. 4 is examples for explaining a Hough transform for a circle wherein

FIG. 5A shows an original image of a sample "house";

FIG. 5B shows an image created by applying a Wavelet transform of x-axis direction to the image shown in FIG. 5A;

DETAILED DESCRIPTION OF THE PREFERRED EMBODIMENTS

Now, the present invention will be described in detail with reference to the accompanying drawings.

The present invention comprises, roughly speaking, two dimensional Wavelet transform means for separating a defect component or portion from a wiring pattern or printed circuit pattern on an image of a wafer pattern and Hough transform means for detecting a position or location and a size of the defect component from a binarization image in which the defect component has been separated from the wiring or printed circuit pattern. Further, in order to improve the defect detection performance by the above means, some other auxiliarily means is utilized.

Since the Hough transform is described in detail in a book entitled "A Basis of Image Recognition [II]" (by Mori & Sakakura, published by Ohm Co., Ltd.), pp. 3–19 only, a brief explanation of the Hough transform process will be given here. The Hough transform is an image processing technique for detecting a specific figure or pattern from a binarization image. A method for detecting a circle from a binarization image will be described here.

A circle is expressed, in an x-y plane (x-y coordinates), by the following equation.

$$(x-a)^2+(y-b)^2=r^2 \tag{1}$$

That is, a circle on an x-y plane is expressed as one point in an (a, b, r) parameter space. An x-y plane is transformed to a parameter space by the Hough transform. In this case, since an x-y plane is transformed to an (a, b, r) space representing features of a circle, the Hough-transform is called a Hough transform for a circle. The Hough transform for a circle is realized by the following equation which is a variation of the equation (1).

$$b=\pm\sqrt{r^2-(x-a)^2}+y \tag{2}$$

Figure 4A:
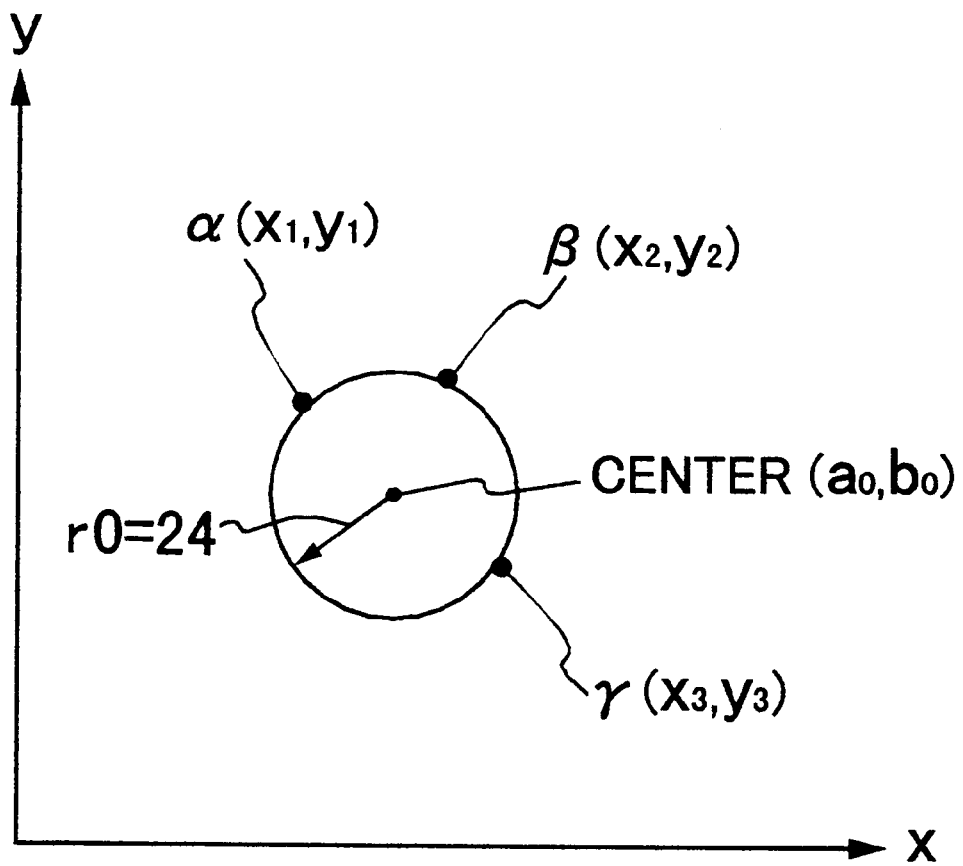
FIG. 4A shows a circle on x-y plane and FIG. 4B shows Hough curves on a-b-r parameter space.
Figure 4B:
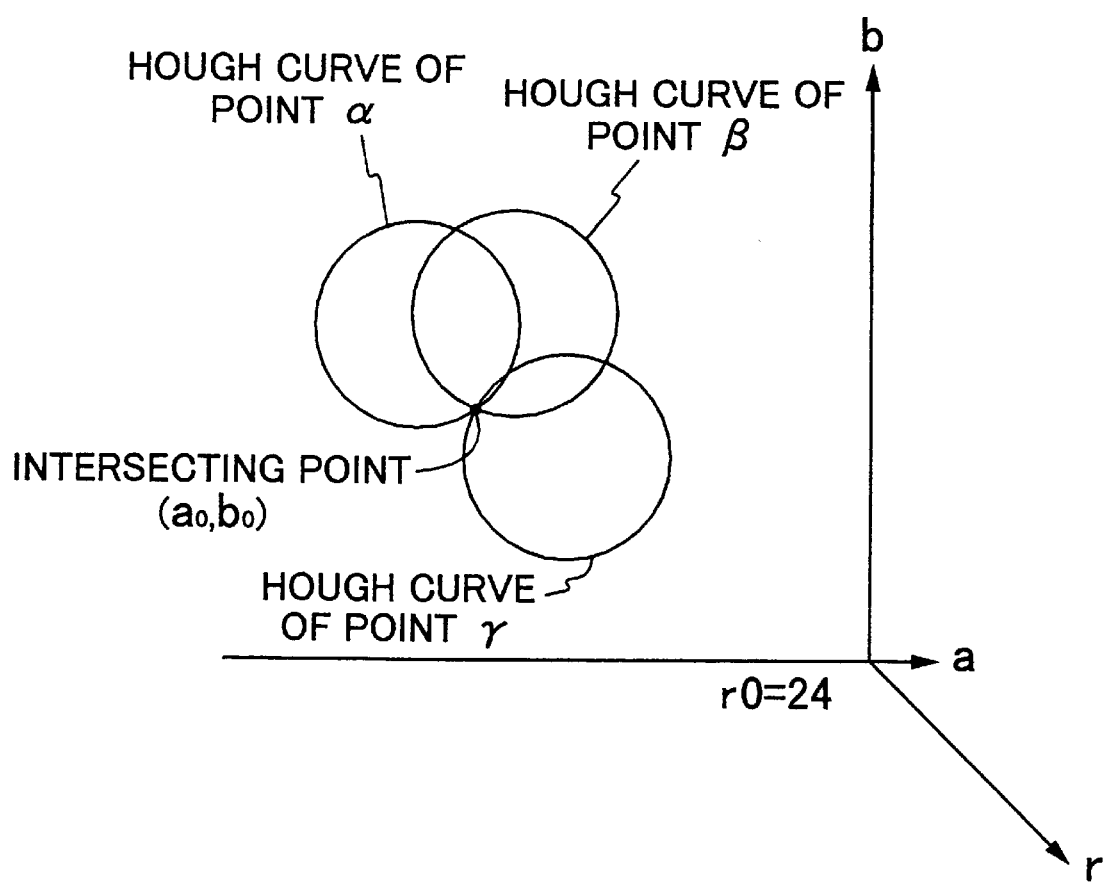

When one point (x0, y0) on an x-y plane is Hough transformed using the equation (2), the point is expressed, in an (a, b, r) parameter space as a circle having a center at point (x0, y0). For example, when three points, α(x1, y1), β(x2, y2) and γ(x3, y3) on an x-y plane shown in FIG. 4A are mapped into an (a, b, r) parameter space (a-b-r coordinates) by the equation (2), a result shown in FIG. 4B is obtained. The parameter space becomes a three dimensional space and an r-axis is perpendicular to an a-b plane. The a-b plane sliced by r=24 is shown in FIG. 4B. With respect to an a-b plane for each r, one point on an x-y plane is transformed to one circle on the a-b plane. The circle obtained by this Hough transform is called a Hough curve. When three points α, β and γ exist on a circle having r0 (in this case, r0=24), the corresponding Hough curves intersect at a point (a0, b0, r0) on the (a, b, r) parameter space. That is, when points exists on a circle on the x-y plane, the circle can be detected in the (a, b, r) parameter space as an intersecting point of many Hough curves. At the intersecting point, the luminance of the intersecting point is increased in proportion to the number of intersecting Hough curves. Therefore, a circle on an x-y plane can be detected by finding parameters having high luminance in the parameter space. In FIG. 4B, only the parameter (a0, b0, 24) has a luminance value 3 and any one of the other parameters has a luminance value equal to 2 or less. By detecting a parameter of (a0, b0, 24) having high luminance, it could be seen that the original three points on an x-y plane are on a circle having the center (a0, b0) and the radius 24.

The Hough transform can fundamentally detect any figure or pattern if the feature of the figure can be expressed by parameters. For example, an ellipse can be detected utilizing a five dimensional parameter space expressed by x-y coordinates (a, b) and (c, d) of two focuses and a sum of distances r from those focuses.

Next, the Wavelet transform is described in detail in a book entitled "An Introduction to WAVELETS" by CHUI, Academic Press, 1992, and hence only a brief explanation of a Wavelet transform process will be given here.

The Wavelet transform for image data is a two dimensional Wavelet transform. This can be realized by combining a one dimensional Wavelet transform for an x-axis direction of the image with a one dimensional Wavelet transform for a y-axis direction of the image. Therefore, a one dimensional Wavelet transform process will be described. While there are many base functions available for effecting the Wavelet transform, the explanation will be given using a Haar-Wavelet base function of the simplest structure. Other Wavelet base functions are of course available, which are different in form of function but provide substantially same output information. The Wavelet transform is composed of a scaling function and a Wavelet function both of which are orthogonal to each other. The scaling function is a function for outputting data smoothing information (low-pass information) and the Wavelet function is a function for outputting detailed information on data (high-pass information). In the case of the Haar Wavelet, the scaling function is $g0=g1=1/2$ and the Wavelet function is $h0=1/2$ and $h1=-1/2$.

When input signals s0–s15 are inputted, output signals t0–t15 resulting from the Haar-Wavelet transform process will be as follows.

$t0=g0\cdot s0+g1\cdot s1$, $t1=g0\cdot s2+g1\cdot s3$, $t2=g0\cdot s4+g1\cdot s5$,

. . . , $t7=g0\cdot s14+g1\cdot s15$, $t8=h0\cdot s0+h1\cdot s1$ $t9=h0\cdot s2+h1\cdot s3$ $t10=h0\cdot s4+h1\cdot s5$

. . . , $t15=h0\cdot s14+h1\cdot s15$

Let's input a specific signal to the Haar-Wavelet transform. For example, the following input signal s is inputted.

$$S(n)=\{0, 0, 0, 0, 0, 0, 0, 2, 2, 2, 2, 2, 2, 2, 2, 2\} \quad (3)$$

In this signal, a big signal change 0→2 occurs at one point. A point where a big signal change occurs like the above signal is called an edge. An edge where the signal value increases as in the equation (3) is called a rising edge and on the contrary, an edge where the signal value decreases is called a falling edge. When the signal of the equation (3) is Haar-Wavelet transformed, the following result t is obtained.

$N\to 0, 1, 2, 3, 4, 5, 6, 7; 8, 9, 10, 11, 12, 13, 14, 15$ $$t(N)=\{0, 0, 0, 1, 2, 2, 2, 2; 0, 0, 0, -1, 0, 0, 0, 0\} \quad (4)$$

(low-pass components) (high-pass components)

The result of the Wavelet transform process are called a Wavelet coefficients. An edge of the input signal s has been detected at a Wavelet coefficient t(11) of the high-pass components. In this manner, an edge component of an input signal can be detected by the Wavelet transform process.

Figure 6:
FIG. 6 shows an image created by applying a Wavelet transform of y-axis direction to the image shown in FIG. 5B.

The Wavelet transform can also be applied to a two dimensional image data such as a SEM image of a wafer pattern. FIGS. 5 and 6 show examples in which the Wavelet transform is specifically applied to image data. In this example, the original image is composed of 512×512 digital data. A one dimensional Wavelet transform is first applied to this image in the x-axis direction. That is, the Wavelet transform operations for 512 signals in the x-axis (lateral axis) direction are repeated 512 times in the y-axis (longitudinal axis) direction. By this process, the images shown in FIG. 5B are obtained. In FIG. 5B, the original image of FIG. 5A is longitudinally divided into two, and low-pass information (L) is disposed in the left side and high-pass information (H) is disposed in the right side.

The same Wavelet transform is applied to the images in FIG. 5B in the y-axis direction. By this process, images shown in FIG. 6 are obtained. In FIG. 6, each of the images of FIG. 5B is laterally divided into two, and low-pass information (L) is disposed in the upper side and high-pass information (H) is disposed in the lower side. Therefore, in FIG. 6, the original image of FIG. 5A is divided into four, and low-pass information in both x-axis and y-axis directions (LL components) is disposed in the upper-left quarter area, combined information of high-pass information in the x-axis direction and low-pass information in the y-axis direction (HL components) is disposed in the upper-right quarter area, combined information of low-pass information in the x-axis direction and high-pass information in the y-axis direction (LH components) is disposed in the lower-left quarter area, and high-pass information in both x-axis and y-axis directions (HH components) is disposed in the lower-right quarter area. That is, the upper-right portion indicates line components in the y-axis direction (longitudinal line components) contained in the original image and the lower-left portion indicates line components in the x-axis direction (lateral line components) contained in the original image. Further, the lower-right portion indicates line components in the inclined direction. In this example, the Wavelet transform is performed first in the x-axis direction, which is followed by the Wavelet transform in the y-axis direction to obtain the image shown in FIG. 6, but even if the Wavelet transform is performed first in the y-axis direction, exactly the same image as shown in FIG. 6 can ultimately be obtained after the two dimensional Wavelet transform process.

Figure 7:
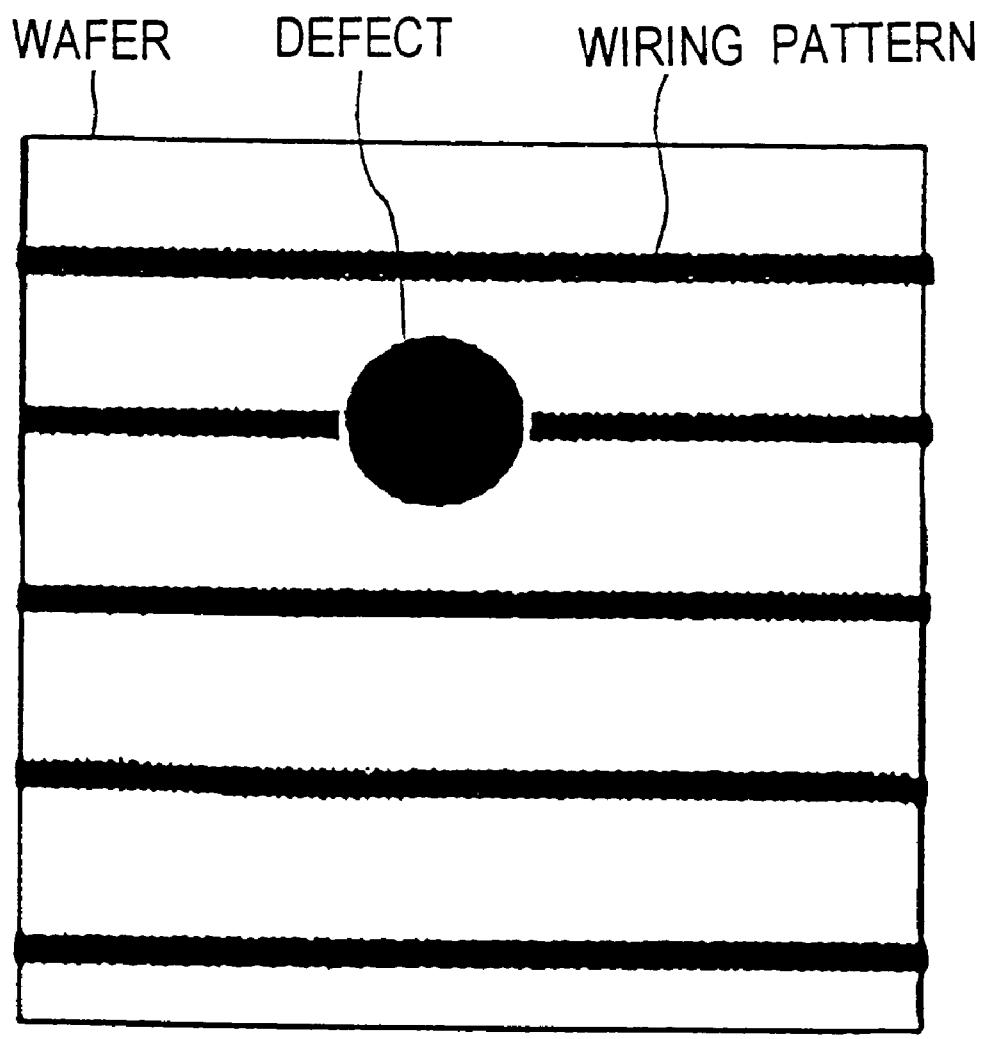
FIG. 7 shows a sample image imitating a semiconductor wafer image.
Figure 8:
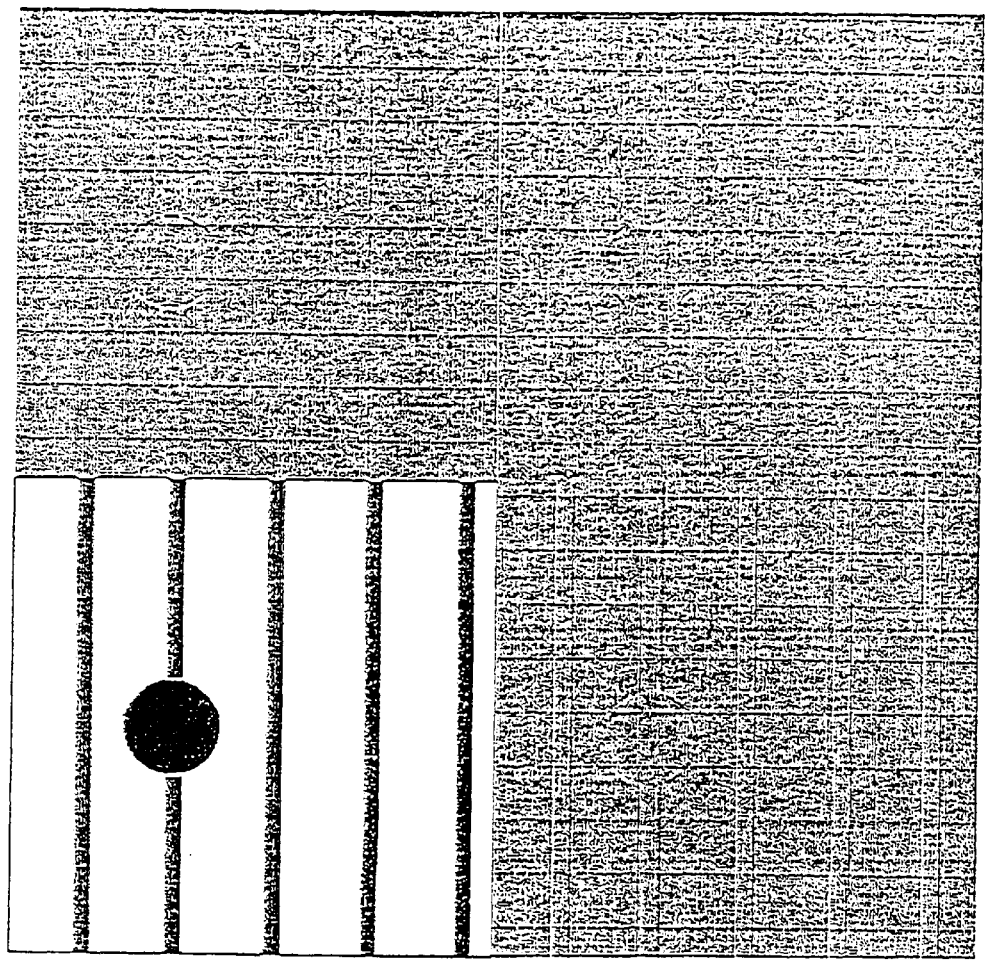
FIG. 8 shows an image created by applying a two dimensional Wavelet transform to the image shown in FIG. 7.

When the two dimensional Wavelet transform having the above characteristics is applied to a semiconductor wafer image having granular defects, the defects can be separated from the background wiring patterns or printed circuit patterns. FIG. 7 is an illustration imitating a semiconductor wafer image in which lateral lines of the image running horizontally correspond to wiring or printed circuit patterns and a black dot located at about the center of one line corresponds to a defect. In such a manner, the wiring patterns are aligned in the lateral direction and/or in the longitudinal direction. When the two dimensional Wavelet transform is applied to such an image, a result shown in FIG. 8 is obtained. Paying attention to the longitudinal line detection components and the lateral line detection components, it is seen that wiring patterns appear in only LH components disposed in the lower-left quarter area. On the other hand, defect components having various direction components are detected in both HL components disposed in the upper-left quarter area and LH components disposed in the lower-left quarter area. In such a way, when the two dimensional Wavelet transform is used, a defect having various direction components can be separated from the wiring patterns having only longitudinal line components or only lateral line components.

When the two dimensional Wavelet transform described above and the Hough transform are combined, a position or location and a size of a defect existing in a semiconductor wafer image can be detected.

Figure 9:
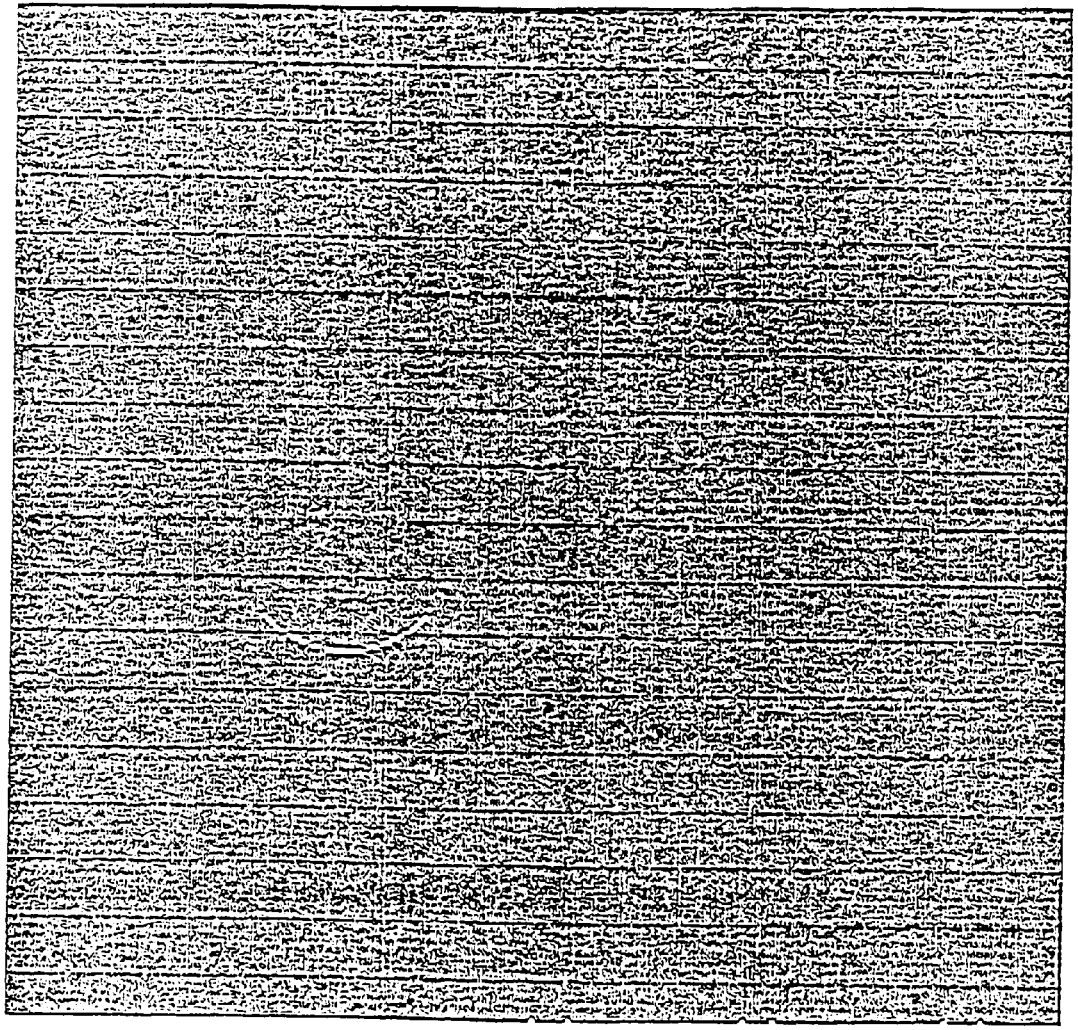
FIG. 9 shows an image created by applying a binarization process to longitudinal line detection components on the upper-right quarter portion of the image shown in FIG. 8.

FIG. 1A is a flow chart for explaining a first basic operation of the image information processing apparatus according to the present invention. In FIG. 1A, first, the two dimensional Wavelet transform S1 is applied to an input image to obtain longitudinal line detection components and lateral line detection components. Each of those component groups has, at an edge portion, a Wavelet coefficient value having a large absolute value and has, at the other portions, Wavelet coefficients values each being equal to or close to zero. A binarization process S2 is performed on the longitudinal line detection components and the lateral line detection components using an appropriate threshold value to create a binarization image having a coefficient value of one (1) at an edge portion and having a coefficient value of zero (0) at a portion other than the edge portion. A Wavelet coefficient at an edge portion has a large absolute value but a positive or a negative value. Since, in a usual binarization process, a negative coefficient becomes zero, when, for example, a usual threshold value process is applied to the longitudinal line detection components shown in upper-right quarter area of FIG. 8, only half of the edges can be detected as shown in FIG. 9. However, the Hough transform can detect the edges even if a portion lacks in the object to be detected. When the Hough transform S3 is applied to the image shown in FIG. 9, in a parameter space, the luminance or brightness of circular components existing in the original image, i.e., parameters corresponding to a defect in a wafer pattern image are increased. By observing the parameter space, a position or location and a size of a defect can be specifically determined.

If some process or processes is added to the processes shown in FIG. 1A, the determination of the position and the size of the defect can be automated.

FIG. 1B is a flow chart for explaining a second basic operation of the image information processing apparatus according to the present invention. In FIG. 1B, a second appropriate binarization process S4 is applied to the parameter space after the Hough transform process S3. In the result of the second binarization process S4, only parameters having large luminance values respectively, i.e., only parameters representing the features of the defect, have, for example, luminance values of "1" respectively and all the other parameters have luminance values of "0" respectively. Therefore, the defect detection becomes easier.

Figure 1C:
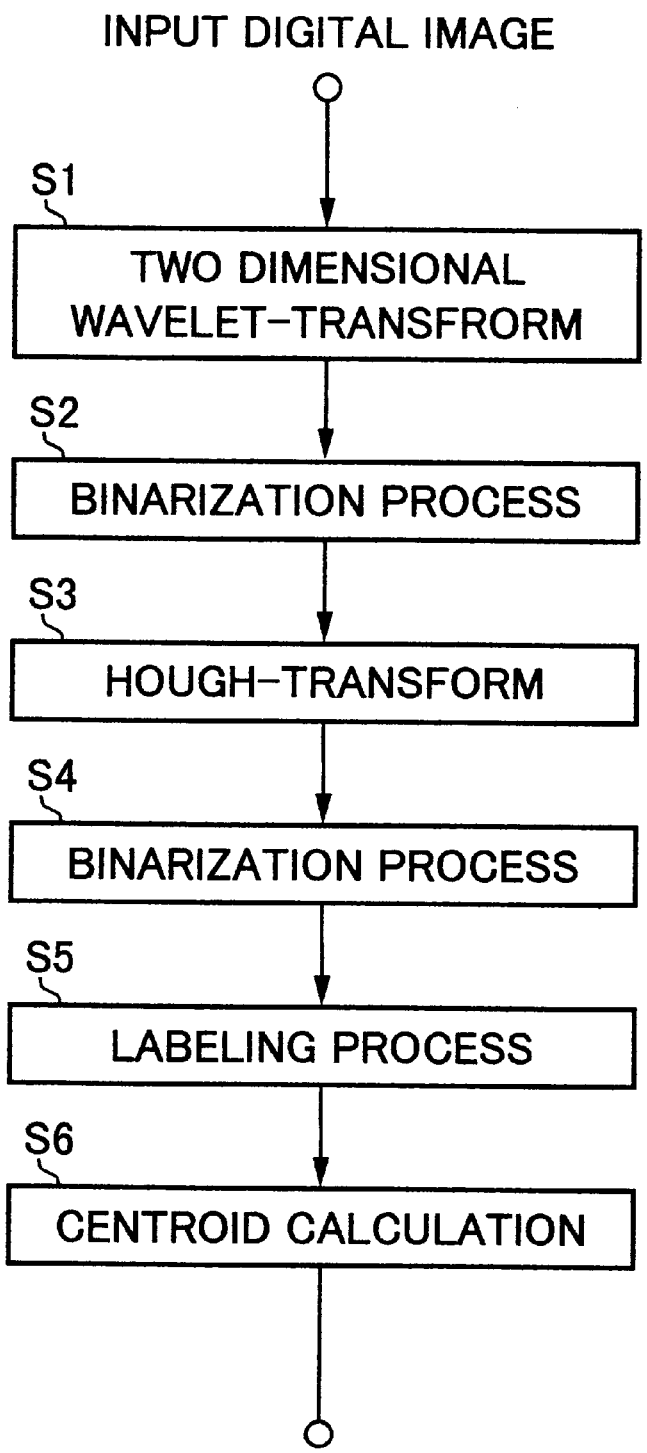
FIG. 1C is a flow chart for explaining a third basic operation of the image information processing apparatus according to the present invention.

FIG. 1C is a flow chart for explaining a third basic operation of the image information processing apparatus according to the present invention. In FIG. 1C, a labeling process S5 for grouping adjacent pixels each having a luminance value of "1" is applied to the result of the binarization process S4 shown in FIG. 1B. Although, in the parameter space after the Hough transform process S3, a luminance value of a parameter of a portion where a pattern of the object to be detected exists is maximized, a luminance value of a parameter of a portion adjacent to the portion of the pattern is also high. Therefore, as the result of the second binarization process S4 shown in FIG. 1B, parameters each having a luminance value of "1" are concentrated in the proximity of a parameter corresponding to the pattern (for example, a circle) of the object to be detected. The portion where parameters each having a luminance value of "1" are concentrated by the labeling process S5 is regarded as a feature parameter for a pattern, and as a representative point of the same label, a mean value of a plurality of the feature parameters is calculated and outputted as a centroid or center of gravity in the center of gravity calculation process S6. By this process, the position and the size of the pattern to be detected can automatically be specified from the input image.

Figure 2A:
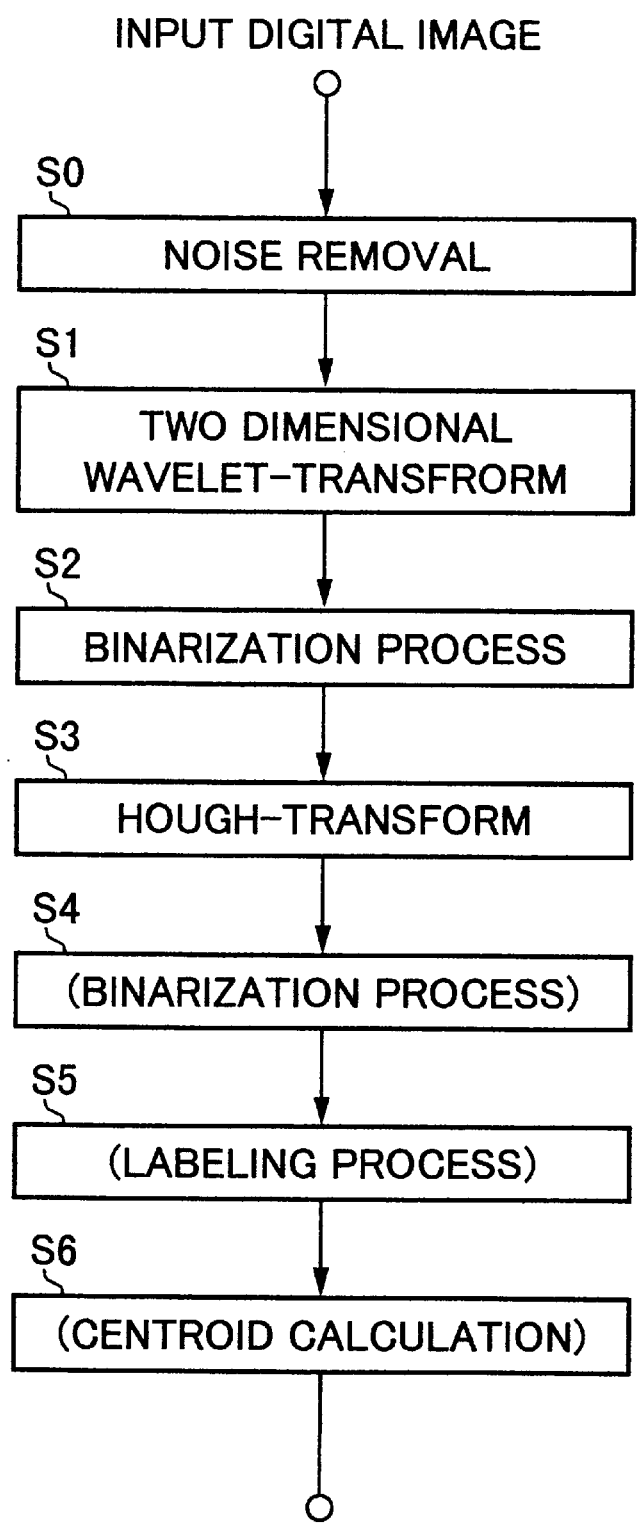
FIG. 2A is a flow chart for explaining a fourth basic operation of the image information processing apparatus according to the present invention.

FIG. 2A is a flow chart for explaining a fourth basic operation of the image information processing apparatus according to the present invention. In FIG. 2A, noise removing process S0 such as a median filter or the like is applied to an input image. Thereafter, the Wavelet transform process S1 and the subsequent processes S1–S3 are performed. If there is a spike shaped noise in the input image, the noise is detected by the Wavelet transform S1 as an edge. If many noises other than a pattern to be detected are Hough transformed, an object not to be detected is erroneously detected. An erroneous detection can be prevented by applying a noise removing filter S0 to the original image. Further, the Hough transform requires a processing time proportional to the number of pixels each having a pixel value of "1" in the binarization image. If a noise removing filter S0 is applied to the input image, the number of Wavelet coefficients each having a pixel value of "1" generated in the Wavelet transform process S1 and the binarization process S2 is decreased and hence the processing speed is also improved. If necessary, the remaining processes S4–S6 may be added thereto.

Figure 2B:
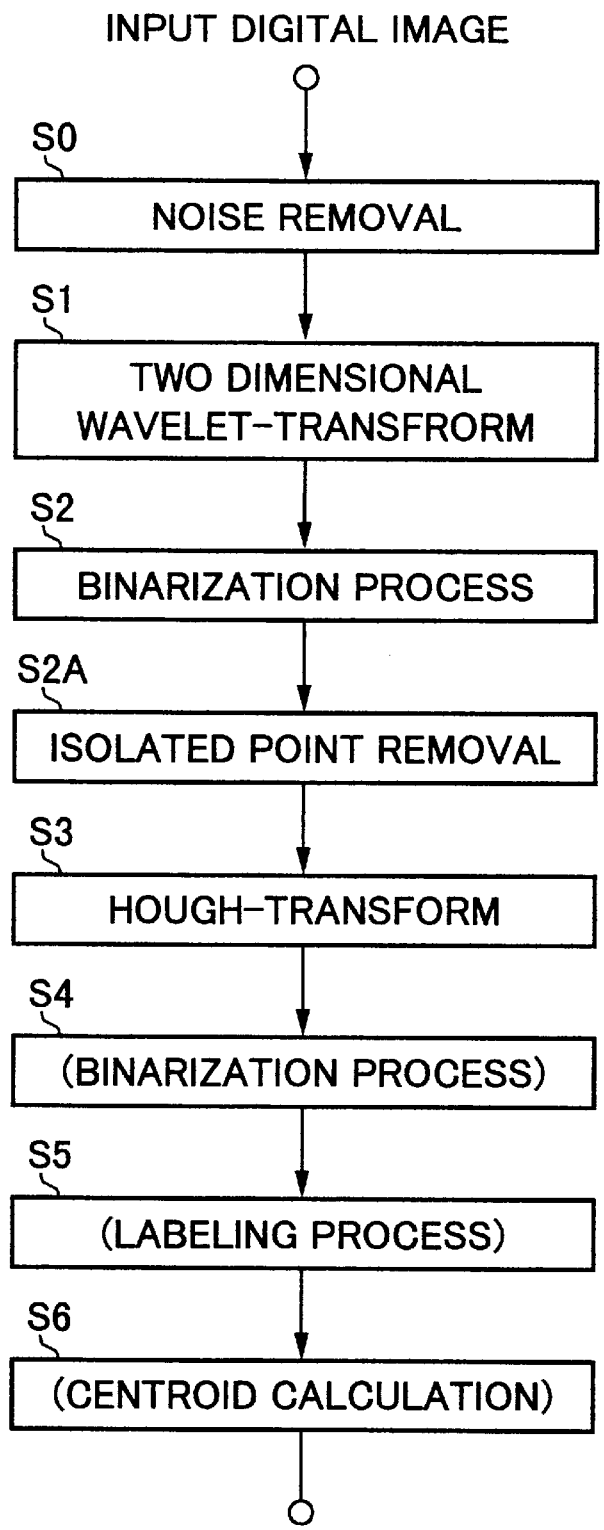
FIG. 2B is a flow chart for explaining a fifth basic operation of the image information processing apparatus according to the present invention.
Figure 10:
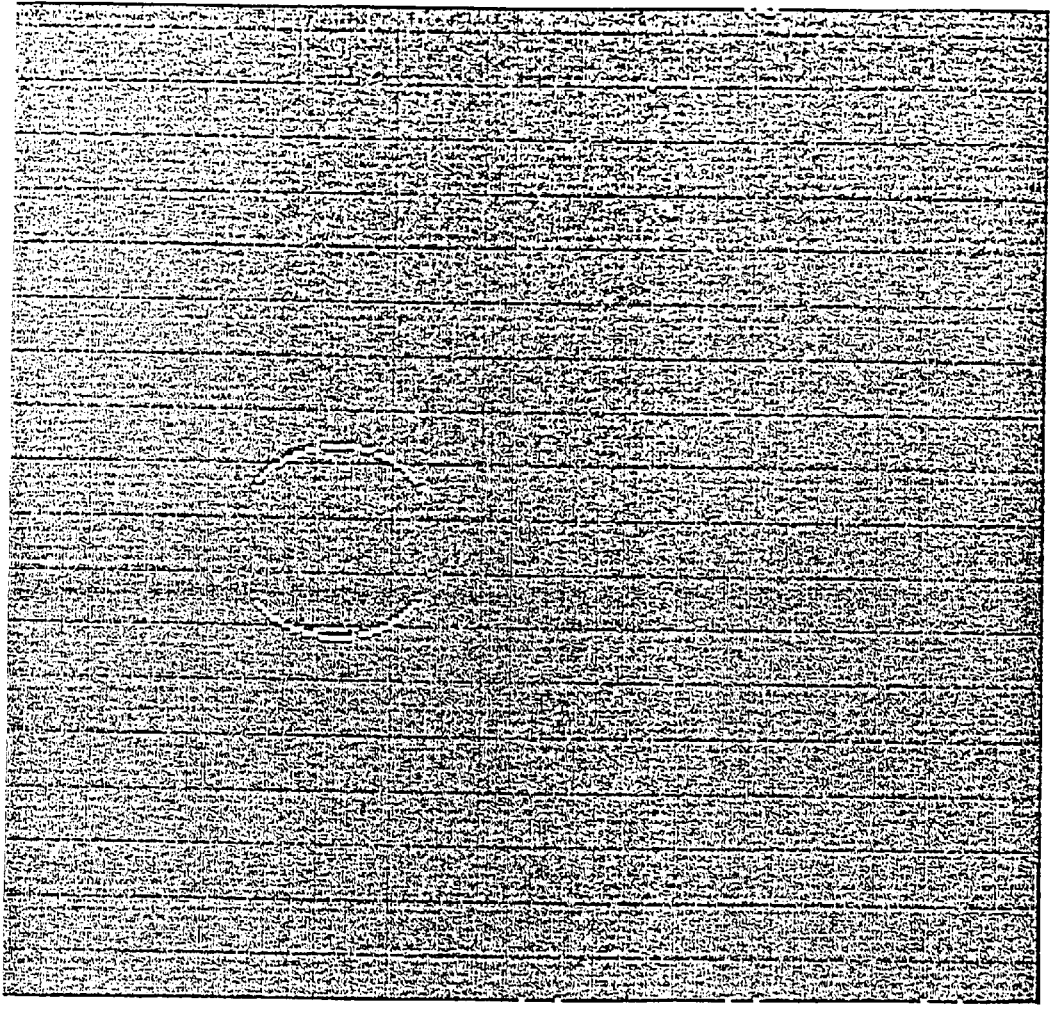
FIG. 10 shows an image created by applying an absolute value binarization process to the longitudinal line detection components on the upper-right quarter portion of the image shown in FIG. 8.

FIG. 2B is a flow chart for explaining a first basic operation of the image information processing apparatus according to the present invention. In FIG. 2B, isolated point removing process S2A is applied, for the purposes of prevention of an erroneous detection and improvement of the processing speed, to the image to which the Wavelet transform process S1 and the binarization process S2 have been applied. This is image processing means for replacing with a pixel having a pixel value "0" a pixel having a pixel value "1" and each of all the pixels adjacent thereto has a pixel value "0" in the binarization image. As shown in FIGS. 9 and 10, in the binarization image after application of the Wavelet transform, Wavelet coefficients each having a value "1" corresponding to the pattern to be detected exist adjacent to each other. Therefore, a coefficient having a value "1" is regarded, if each of all the coefficients surrounding it has a value "0", as a noise and treated as value "0". By this process, prevention of an erroneous detection and improvement of the processing speed can be realized.

Figure 2C:
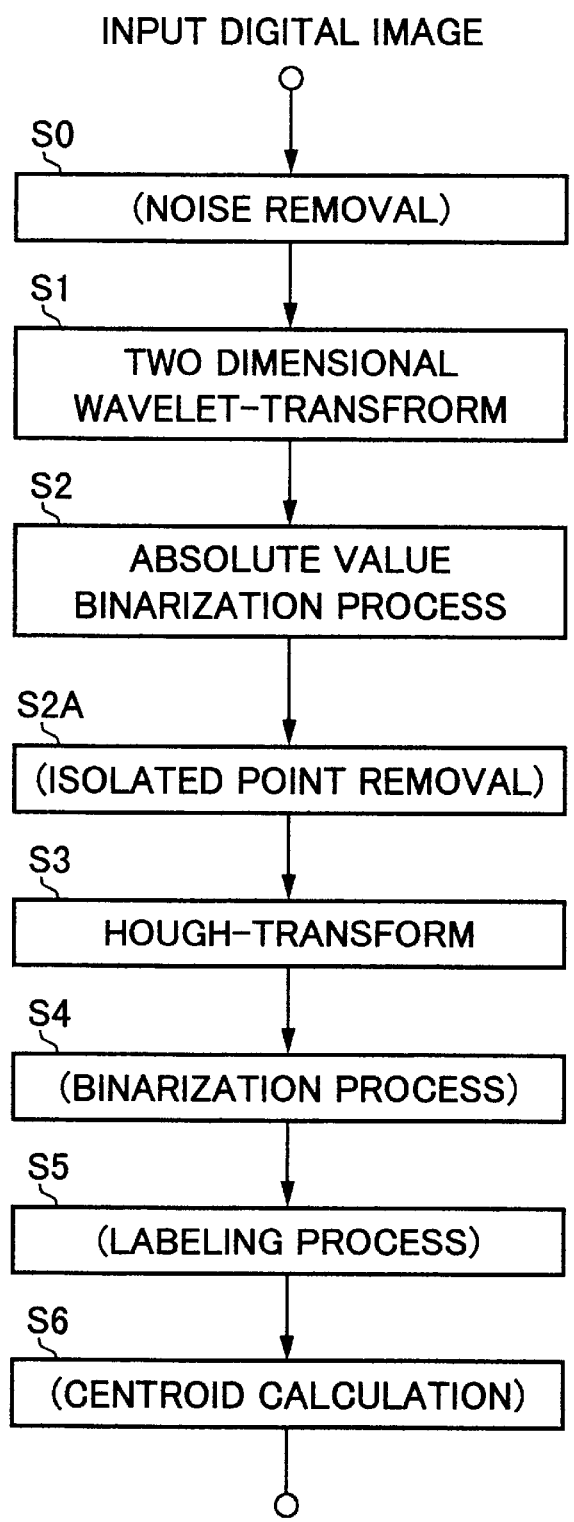
FIG. 2C is a flow chart for explaining a sixth basic operation of the image information processing apparatus according to the present invention.

FIG. 2C is a flow chart for explaining a first basic operation of the image information processing apparatus according to the present invention. In FIG. 2C, a binarization process S2 is applied, considering that a coefficient value at an edge portion may become negative in the Wavelet transform S1, to the absolute values of Wavelet coefficients instead of the usual binarization process. If the binarization process S2 for the absolute value is applied to the longitudinal line detection components in the upper-right quarter area of FIG. 8, all the edges can be detected as shown in FIG. 10. By applying the Hough transform S3 to this, the parameter luminance corresponding to a defect becomes larger than that in the case of utilizing the usual binarization process and hence the detection becomes easy.

Figure 3A:
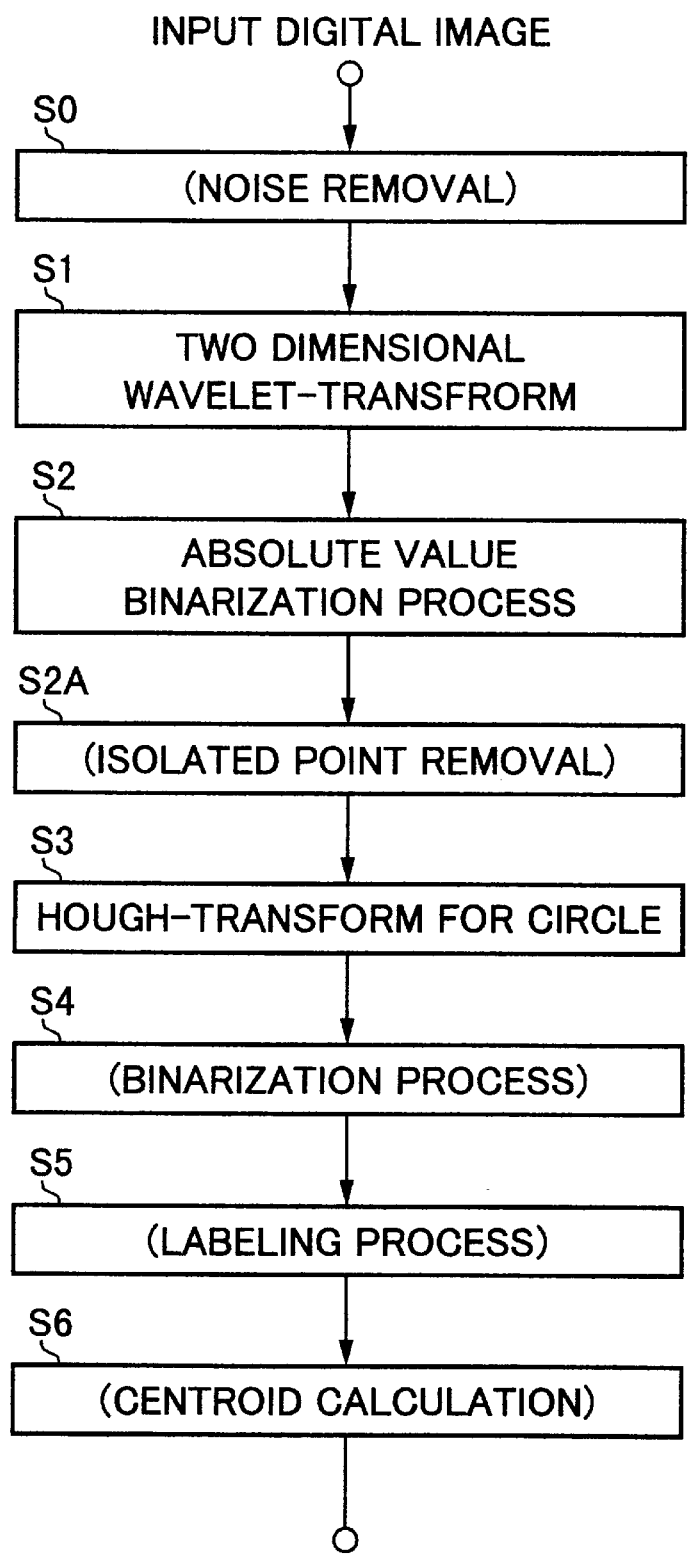
FIG. 3A is a flow chart for explaining a seventh basic operation of the image information processing apparatus according to the present invention.

FIG. 3A is a flow chart for explaining a seventh basic operation of the image information processing apparatus according to the present invention. In FIG. 3A, a pattern to be detected using the Hough transform S3 for detecting a pattern is especially limited to a circle. For example, in the Hough transform for detecting an ellipse, the parameter space becomes a five dimensional space and hence the speed of the detection process following it becomes slow. In the Hough transform for a circle S3, the parameter space is a three dimensional space. Therefore, the Hough transform for a circle S3 can detect a defect at higher speed compared with the Hough transform for other figures or patterns such as an ellipse.

In addition, the Hough transform S3 may be applied to both of the binarization images corresponding to the longitudinal line detection components and the lateral line detection components resulted by the Wavelet transform process S1, and the results of the two Hough transform operations are overlapped in the same parameter space. Since the figure to be detected appears in both longitudinal line detection components and lateral line detection components, the figure can surely be detected by this method.

However, in case of wafer pattern image, a wiring pattern appears in either longitudinal line detection components or lateral line detection components. If the Hough transform is applied to those images, there will be a possibility to erroneously detect an object other than the object to be detected.

Accordingly, in FIG. 3A, the longitudinal line detection components and the lateral line detection components resulted by the Wavelet transform process S1 may be observed to apply the Hough transform S3 only to one group of the longitudinal line detection components or the longitudinal line detection components. As shown in FIGS. 7 and 8, the wiring pattern in a semiconductor wafer image is aligned in the longitudinal direction or in the lateral direction and hence appears in either of the longitudinal line detection components or the longitudinal line detection components. If the Hough transform is applied only to the components where the wiring pattern does not appear, an only object to be detected can be Hough transformed and the object can surely be detected. The remaining processes S0, S2A, S4–S6 in FIG. 3A may be added thereto, if necessary.

Figure 3B:
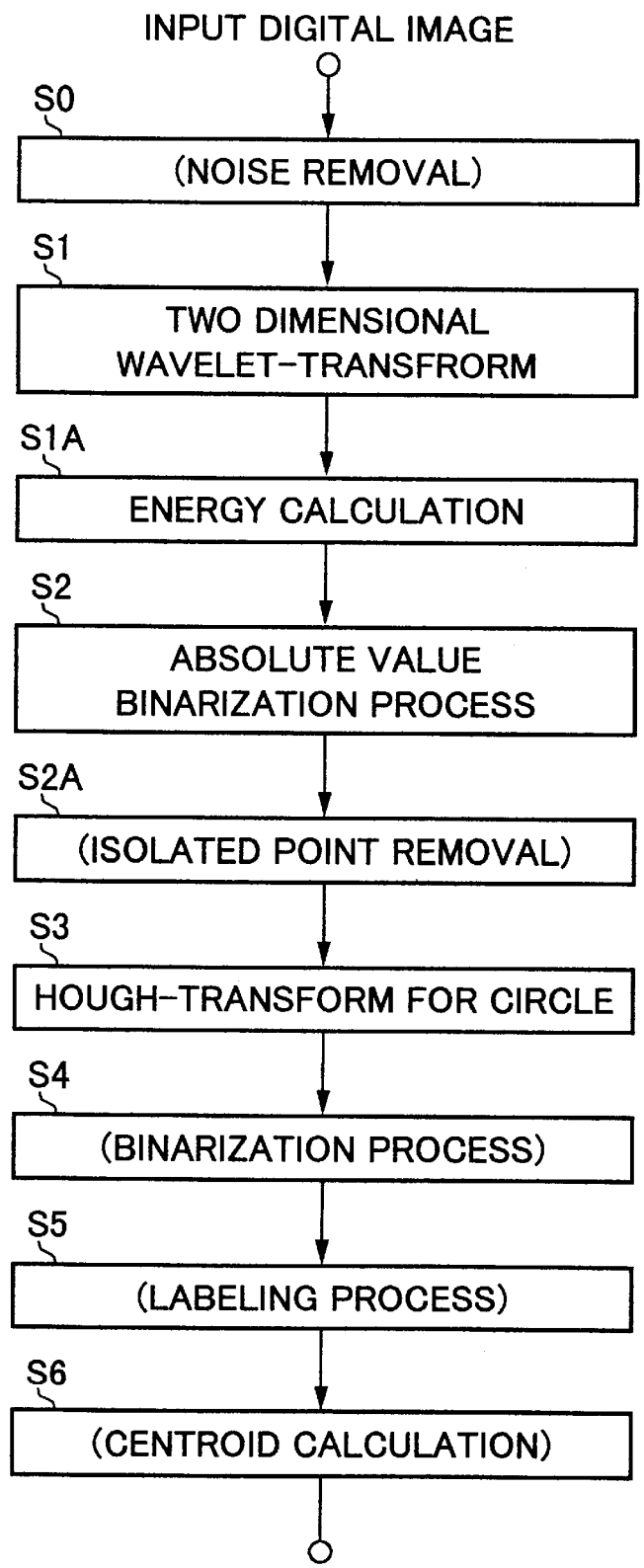
FIG. 3B is a flow chart for explaining a eighth basic operation of the image information processing apparatus according to the present invention.

FIG. 3B is a flow chart for explaining an eighth basic operation of the image information processing apparatus according to the present invention. In FIG. 3B, there is added to the processes shown in FIG. 3A a process (energy calculation process) S1A for automatically determining whether the Hough transform S3 is applied to the longitudinal line detection components or the lateral line detection components. In FIG. 8, the wiring patterns and the defect appear in the lateral line detection components in the lower-right quarter area, and the only defect appears in the longitudinal line detection components in the upper-right quarter area. An absolute value of a Wavelet coefficient is large at a portion where an edge is detected but has a value close to zero at the other portion. Therefore, degrees of edge component detection are quantified for the longitudinal line detection components and the lateral line detection components, respectively and these degrees are compared with each other. The smaller degree of edge detection is regarded to represent the line detection components where a wiring pattern is not detected. By applying the Hough transform to the line detection components, i.e., by applying the Hough transform only to the longitudinal line detection components in the upper-right quarter area in FIG. 8, the pattern to be detected can be detected. As a method of quantifying the degree of edge detection, the energy of a Wavelet coefficient is defined in the process S1A. This is defined by equation (5) when each Wavelet coefficient is W (s, t), the number of two dimensional Wavelet coefficients in the x-axis direction is M and the number of two dimensional coefficients in the y-axis direction is N.

$$E = \frac{1}{MN} \sum_{s=1}^{M} \sum_{t=1}^{N} W(s, t) \qquad (5)$$

The remaining processes S0, S2A, S4–S6 in FIG. 3B may be added thereto, if necessary.

In the basic operation shown in FIG. 3A, the binarization threshold value to be applied to the result of the process of the Hough transform for a circle S3 is changed in accordance with the magnitude of the radius r. For example, if, in the original image, there are a circle C1 having its center (a, b) and its radius 10 and a circle C2 having its center (c, d) and its radius 100, in the parameter space, the luminance value of a parameter (a, b, 10) corresponding to C1 is approximately 10×2×π≈63, and the luminance value of a parameter (c, d, 100) corresponding to C2 is approximately 630. In such a manner, the luminance value of the parameter changes significantly depending on the magnitude of the radius. By changing the binarization threshold value in proportion to the radius parameter r, a circle having an arbitrary magnitude of radius can be detected.

Figure 3C:
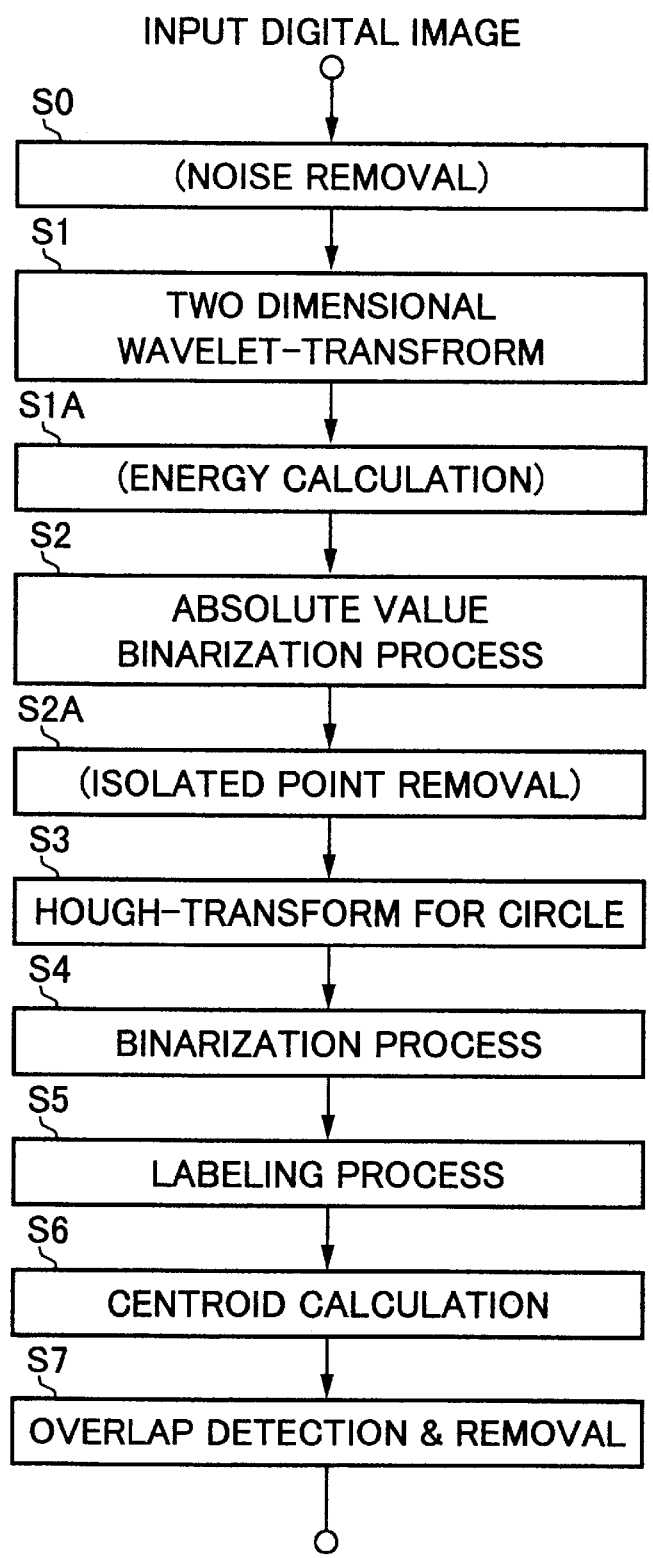
FIG. 3C is a flow chart for explaining a ninth basic operation of the image information processing apparatus according to the present invention.

FIG. 3C is a flow chart for explaining a ninth basic operation of the image information processing apparatus according to the present invention. In FIG. 3C, if a plurality of circles are detected during the processing shown in FIG. 3A, a check is made to see whether those circles overlap with each other in an x-y plane or not in the processes S4–S7. For example, there may be a case in which a noise component is added to an arc of a circle existing on an x-y plane and a circle slightly smaller than that circle is detected. A detection of a plurality of defects at similar positions is judged to be an erroneous detection. In this case, the larger circle is only detected and even if a smaller circle overlapping therewith is detected, this smaller circle is excluded. Specifically speaking, in FIG. 3C, when a plurality of circles are detected, a check is made to see whether the center of the smaller circle is within the larger circle or not, and if the center of the smaller circle is within the larger circle, the smaller circle is excluded from the detection. By adding such processing, the above check operation is realized. The remaining processes S0, S1A and S2A in FIG. 3B may be added thereto, if necessary.

Figure 11:
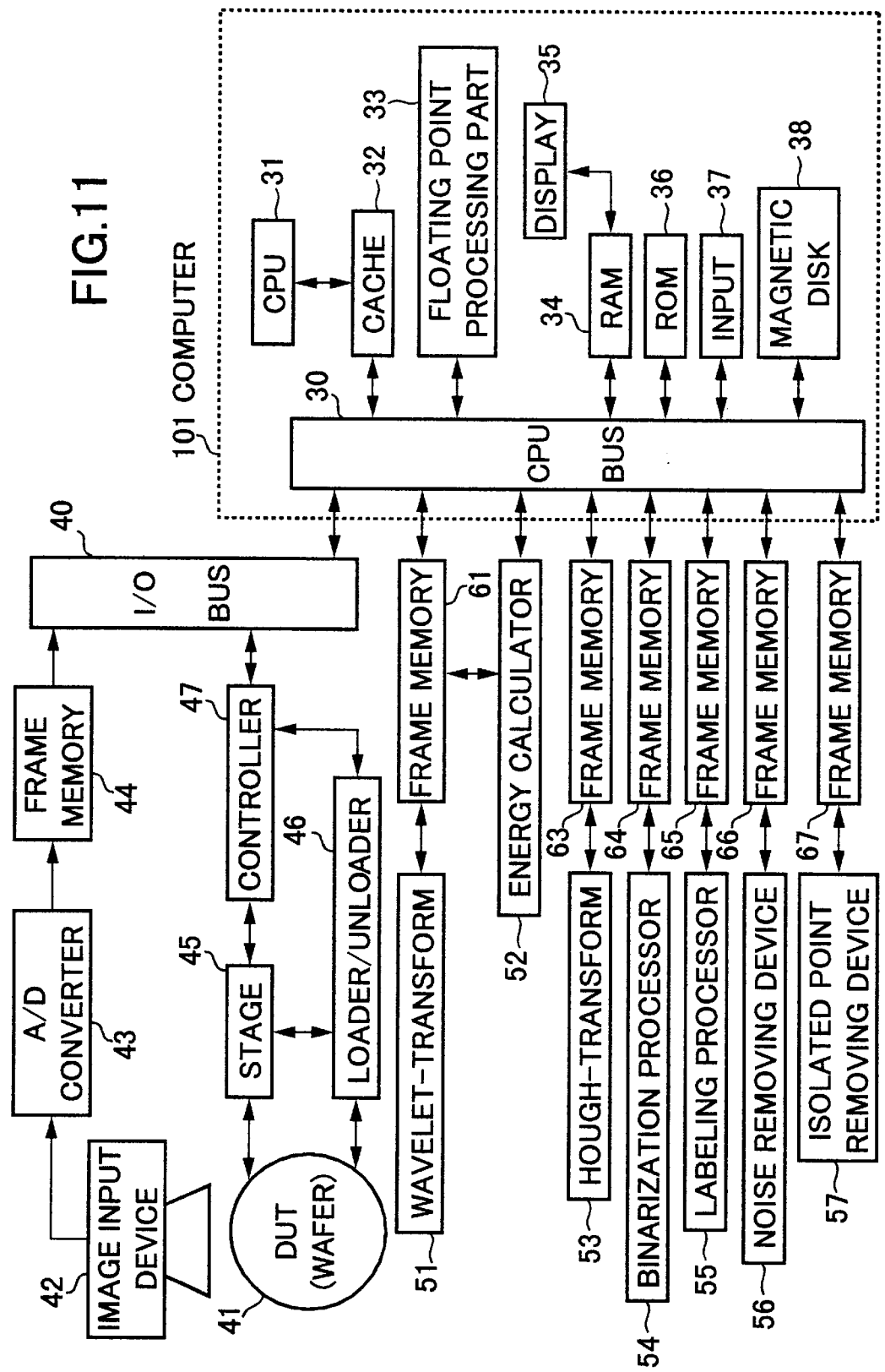
FIG. 11 is a block diagram showing a first embodiment of the image information processing apparatus according to the present invention.

FIG. 11 is a block diagram showing the construction of a first embodiment of the image information processing apparatus according to the present invention. A computer 101 comprises a CPU 31 for performing input/output operations and calculations, a cache 32 for storing therein instructions and data to be used frequently to speed up the process, a floating point calculation part 33, a RAM 34 for storing therein data inputted by a user and the other data, a ROM 36 for storing therein a system program, a display device 35 for displaying a user selection menu or calculation results, an input device 37 such as a keyboard or a pointing device (mouse or the like) for inputting a parameter or a command, and a magnetic disk drive 38 for storing the calculation results etc.

Figure 14:
FIG. 14 shows a SEM image of a semiconductor wafer pattern which is an input image.

A DUT (a device under test) 41 such as a semiconductor wafer or the like to be inspected is loaded on or unloaded from a stage 45 by a loader/unloader 46. An image of a DUT loaded is inputted by an image input device 42 such as an election microscope and is digitized by an A/D converter 43. The digitized image is stored in a frame memory 44 or is transferred to the RAM 34 in the computer. FIG. 14 is a digital image of a wafer pattern inputted by a scanning type electron microscope (SEM). This digital image has, for example, a resolution of 512×512 pixels and 256 levels of gray scale.

With respect to this image, a position or location and a size of a defect are detected. Here, the processings as shown in FIG. 3B and FIG. 3C will be explained. All the processings performed in the remaining basic operations as shown in FIGS. 1A–1C, 2A–2C and 3A are included in the processings performed in the basic operations as shown in FIGS. 3B and 3C.

The image data stored in the frame memory 44 or the RAM 34 is transferred first to a frame memory 66 as an input image data. Noise removing means 56 for performing, for example, a median filtering process is applied to the input image data in the frame memory 66 to remove noises from the input image data. The input image data from which noises have been removed is transferred to a frame memory 61. Then the two dimensional Wavelet transform is applied to this image data by the Wavelet transform means 51. Thus, the result shown in FIG. 15 is obtained.

Figure 15:
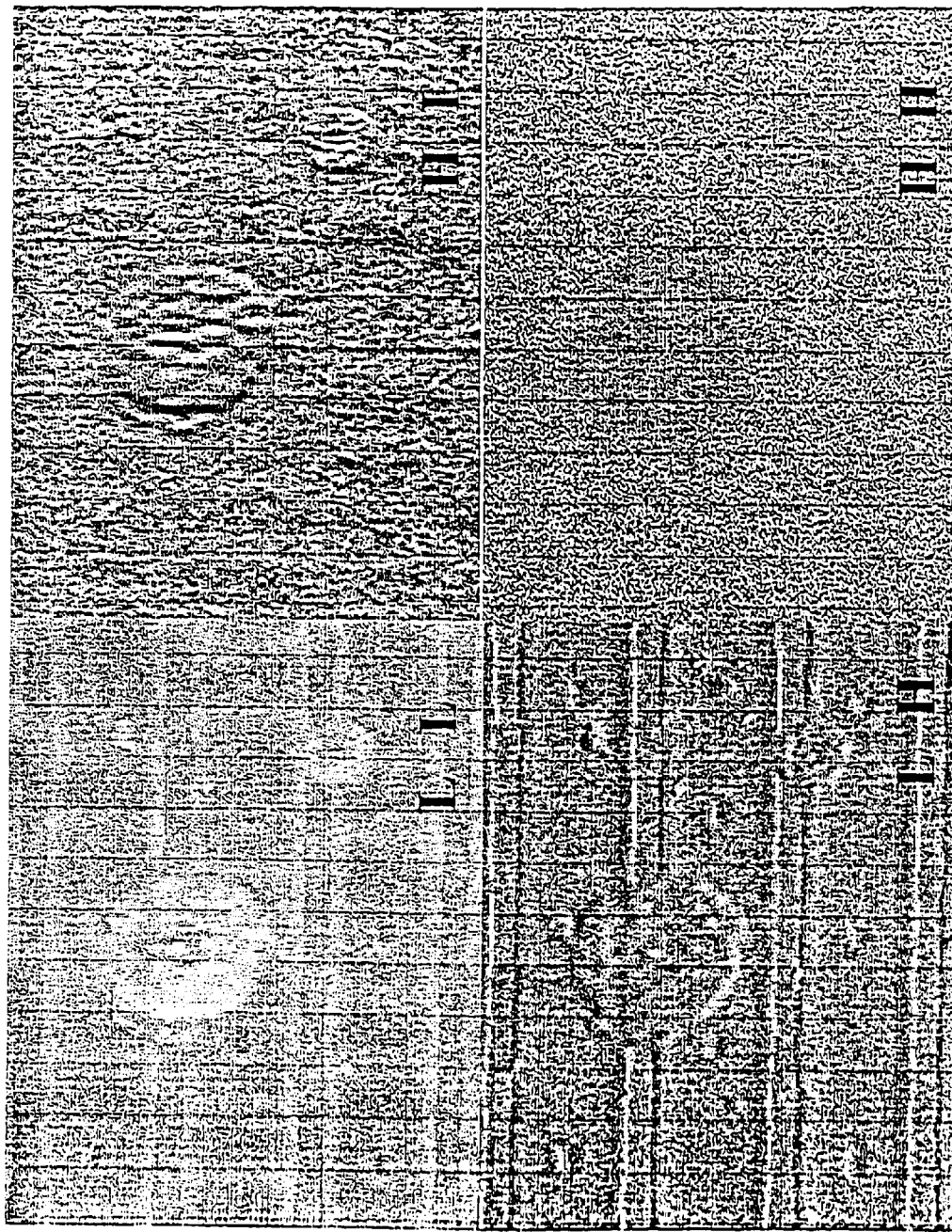
FIG. 15 shows an image created by applying a two dimensional Wavelet transform to the image shown in FIG. 14.
Figure 16:
FIG. 16 shows an image created by applying an absolute value binarization process to the longitudinal line detection components on the upper-right quarter portion of the image shown in FIG. 15.

In FIG. 15, an energy of the longitudinal line detection components (HL) in the upper-right quarter area and an energy of the lateral line detection components (LH) in the lower-left quarter area are calculated by the energy calculating means 52 and those calculated energies are compared with each other. In the case of FIG. 15, the energy of the longitudinal line detection components is 5.32 and the energy of the lateral line detection components is 10.69. Since the energy of the longitudinal line detection components is lower than the other, the process after this will be performed for the longitudinal line detection components. The longitudinal line detection components are transferred to a frame memory 64. In this case, a binarization process is applied to the absolute value of the Wavelet coefficient by the binarization processing means 54. Thus, a binarization image as shown in FIG. 16 is obtained. Here, as the threshold values, ±5 are set experientially.

Figure 17:
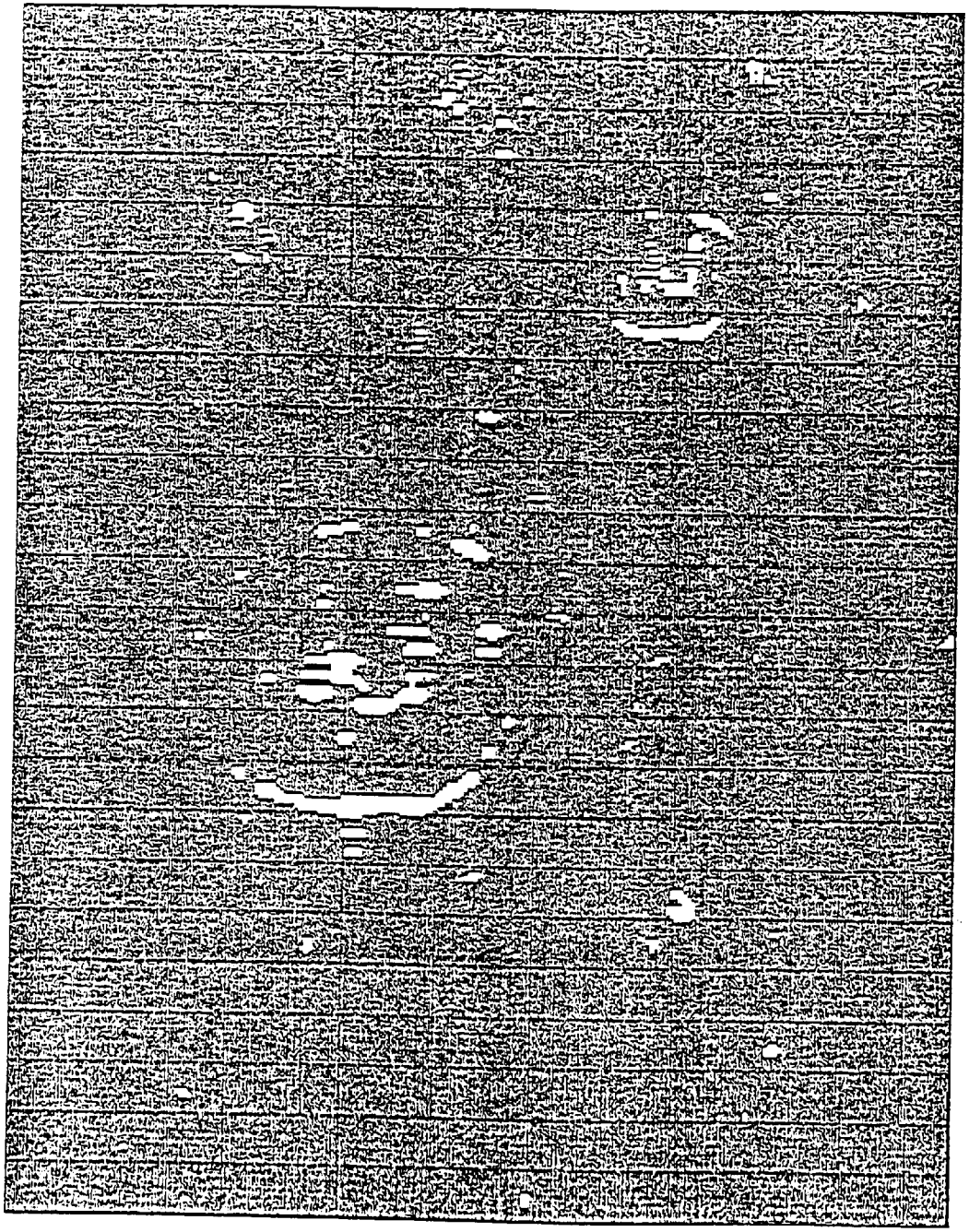
FIG. 17 shows an image created by applying an isolated point removing process to the image shown in FIG. 16.

When this image is transferred to a frame memory 67 and the isolated point removing means 57 is applied thereto, the result shown in FIG. 17 is obtained.

Figure 18:
FIG. 18 shows an image on a-b plane in case of r=40 which is created by applying a Hough transform for a circle to the image shown in FIG. 17.

Next, the obtained result is transferred to a frame memory 63 and here, the Hough transform means 53 for detecting a circle is applied to the obtained result. The parameter space is a three dimensional space of (a, b, r). FIG. 18 shows an image in an (a, b) parameter plane for r=40.

Figure 19:
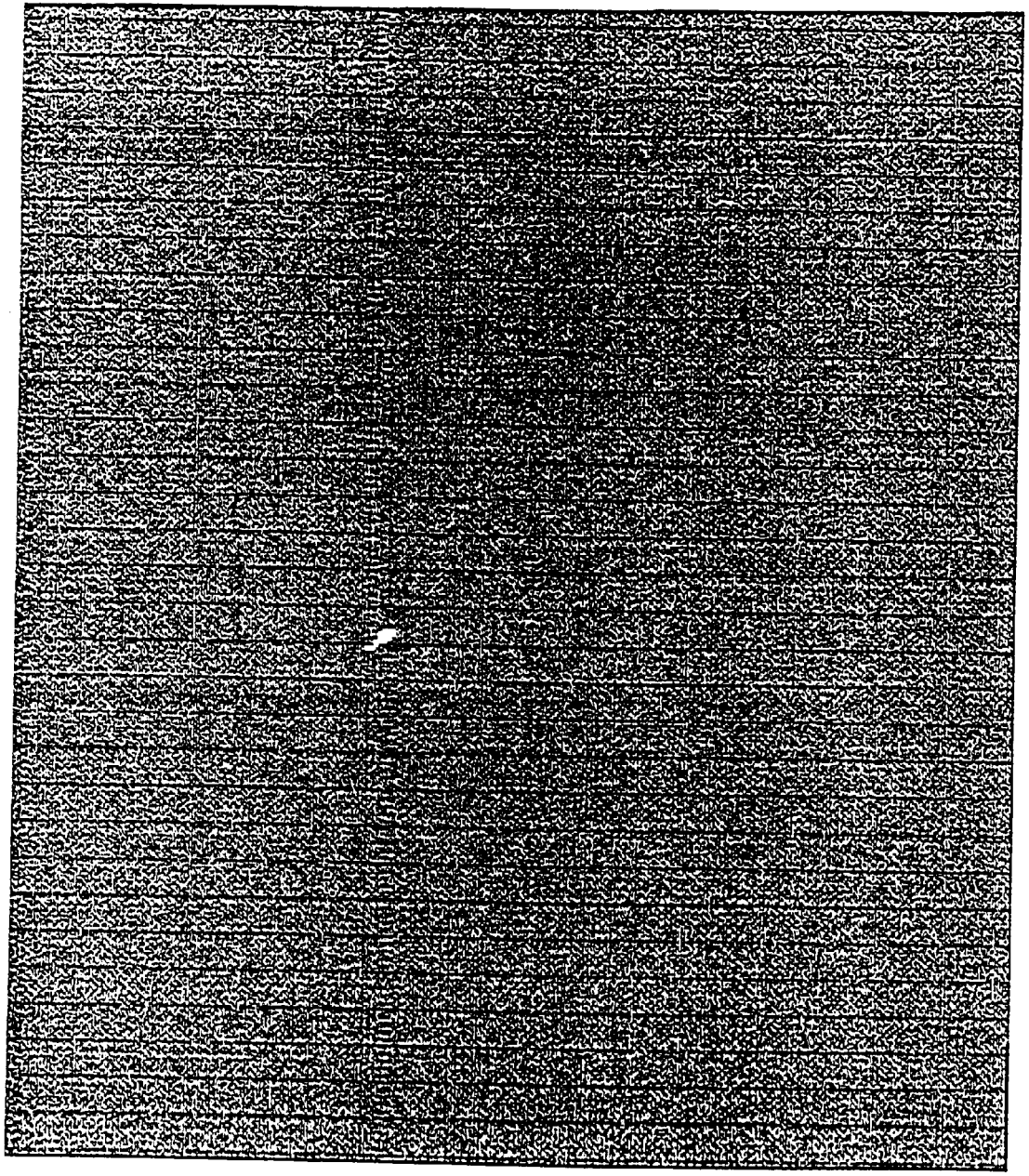
FIG. 19 shows an image created by applying a binarization process to the image shown in FIG. 18.

This three dimensional parameter is transferred to the frame memory 64 and the binarization processing means 54 is applied to this three dimensional parameter. In this case the binarization threshold value is changed in accordance with the r. If a circle having a center (a0, b0) and a radius r exists in an x-y plane in a complete shape, the parameter luminance is $2\pi r0$. Therefore, if, for example, a threshold value is set to $\pi r0$, the parameter luminance exceeds the threshold value even though the circle having a radius r lacks its half portion. If a threshold value process is applied to the image data shown in FIG. 18, a group of pixels each having a luminance value "1" i.e., a group of white pixels appears as shown in FIG. 19. This result is transferred to a frame memory 65 and the labeling processing means 55 is applied thereto. As a result of the labeling process, a plurality of parameter coordinates a and b belong to each label (in the example of FIG. 19, the number of labels is 1). A mean value a' of coordinates a and a mean value b' of coordinates b are calculated to obtain the mean value coordinates (a', b'). The mean value coordinates are the coordinates of a centroid. The centroid coordinates are determined to be the x and y coordinates of a center of a detected circle. Thus, radius information (in the case of FIG. 19, r=40), a and b coordinates of the centroid (146, 152) are stored in the RAM 34.

Figure 20:
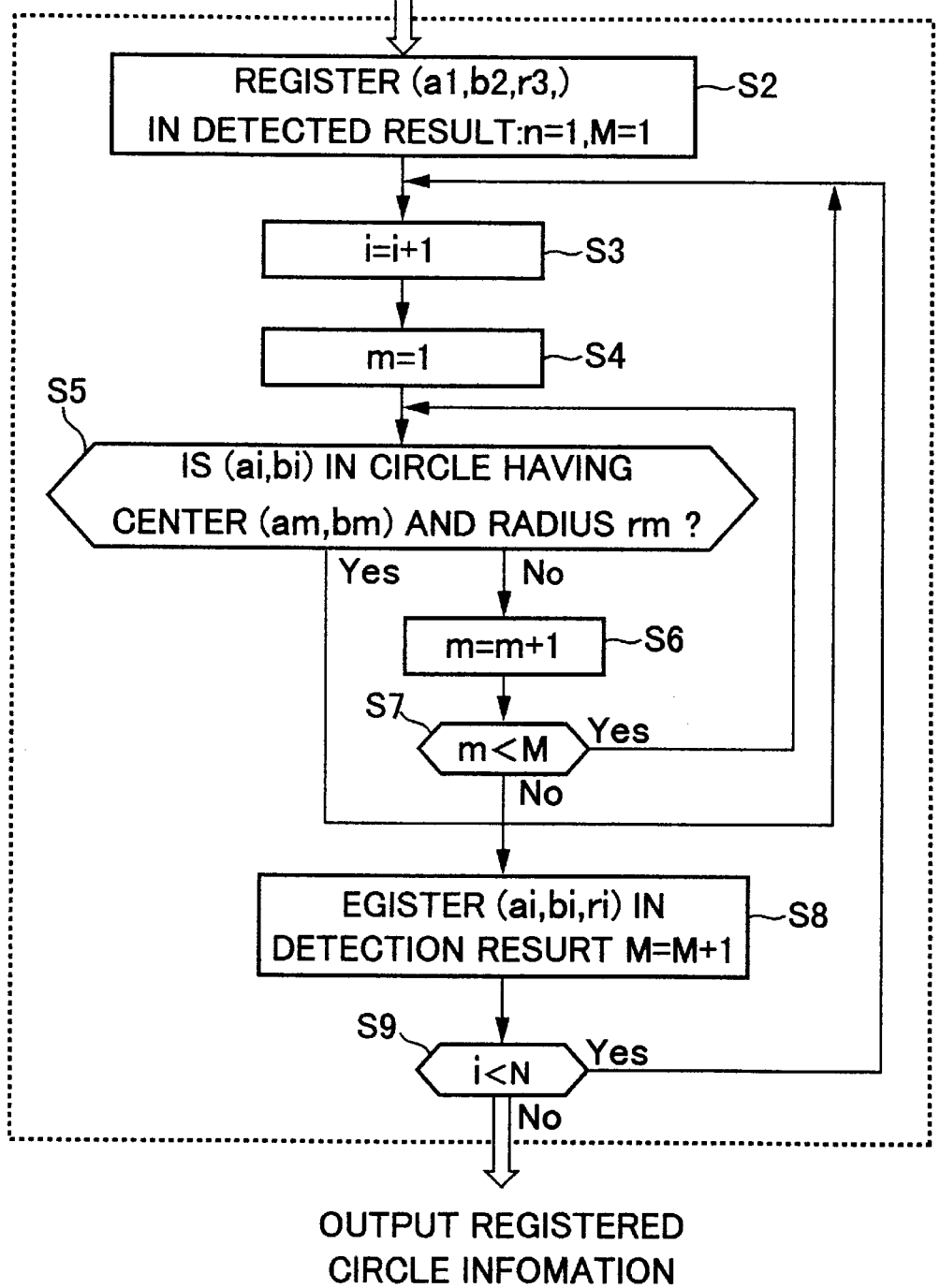
FIG. 20 is a flow chart for explaining an overlap detection removing process performed in the ninth basic operation shown in FIG. 3C.

The overlap detection removing means is applied to this result. FIG. 20 shows a flow chart showing the processing effected by the overlap detection removing means. The function of the overlap detection removing means is performed by the computer 101. A circle having the largest radius among the circles detected by the above process from the sample data shown in FIG. 14 is the circle having a center (146,152) and a radius 40 detected as shown in FIG. 19. This circle is registered in the RAM 34 as a final detection result. Then a circle having a center (147, 154) and a radius 35 is also detected. This circle overlaps with the already detected circle having a center (146, 152) and a radius 40. In order to remove such an overlapping circle, a check is made to see if the center of a circle detected at second time and after is not in the circle previously detected. If the center of the circle detected later is in the circle previously detected, the circle detected later is excluded from the detected circles. By repeating this process, the circles overlapping with the circle detected at the first time are all removed, and at the second time, a circle having a center (252, 71) and a radius 15 is detected. The other detected circle are excluded since those circles overlap with either one of the two detected circles.

By the above processes, a position (x, y) and a size r of a defect can automatically be detected. In the example mentioned above, a defect having x and y coordinates (146, 152) and a size r=40 and a defect having x and y coordinates (252, 71) and a size r=15 are detected.

Figure 12:
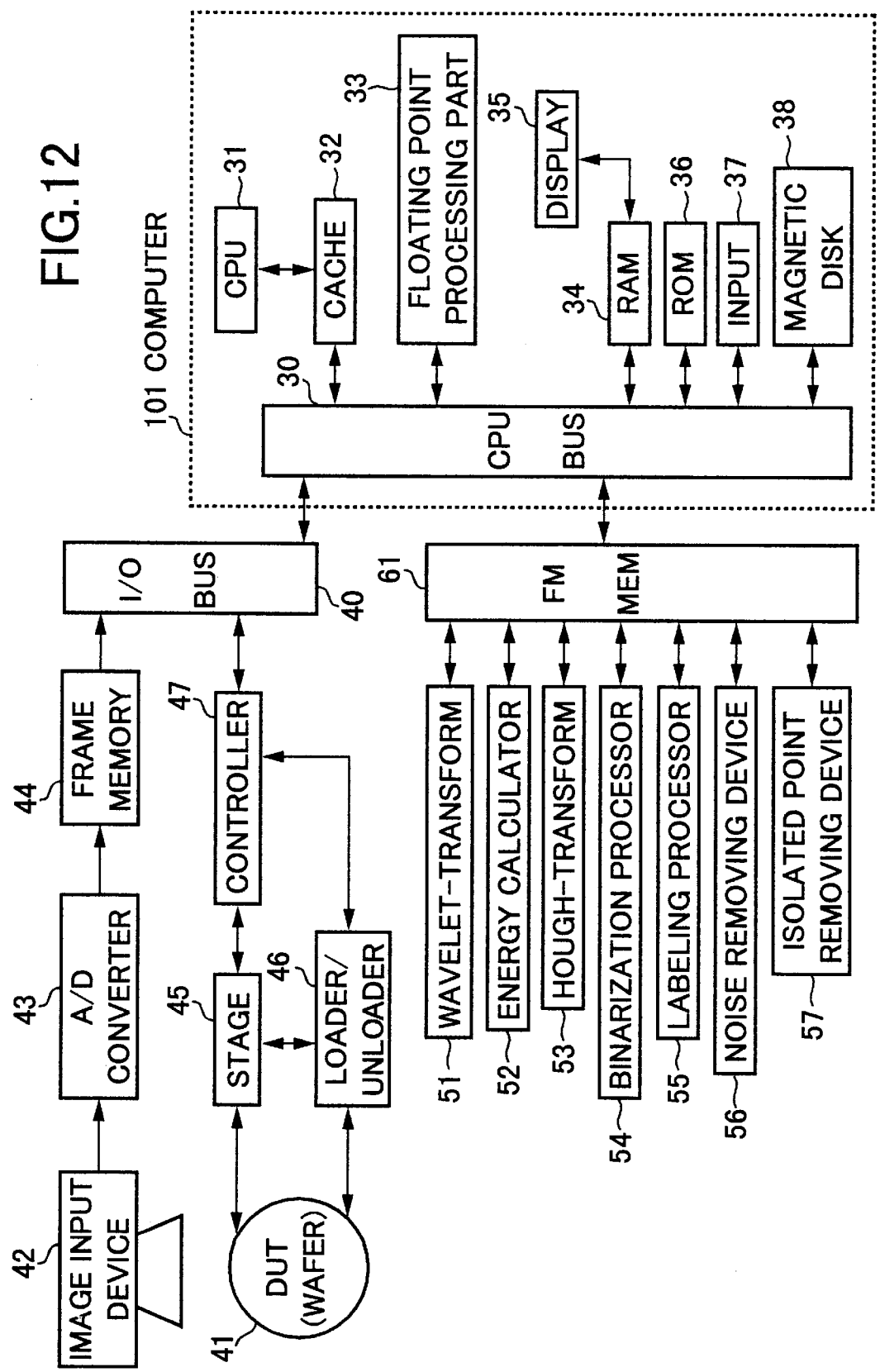
FIG. 12 is a block diagram showing a second embodiment of the image information processing apparatus according to the present invention.

FIG. 12 is a block diagram showing the construction of a second embodiment of the image information processing apparatus according to the present invention. While a dedicated frame memory is provided for each processing means in FIG. 11, the apparatus shown in FIG. 12 is intended to reduce the amount of memory and to improve memory efficiency by commonly using a frame memory.

Figure 13:
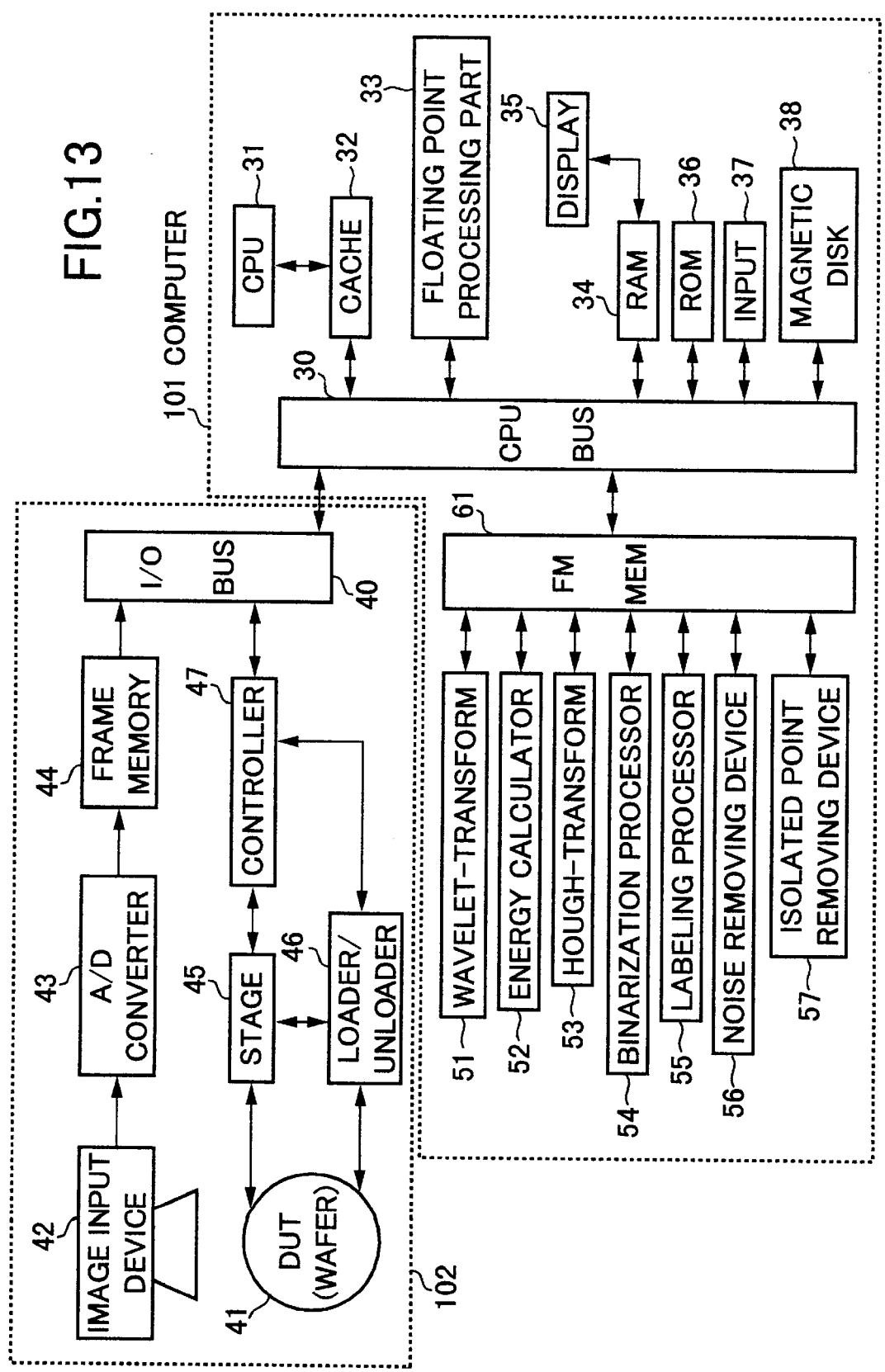
FIG. 13 is a block diagram showing a third embodiment of the image information processing apparatus according to the present invention.

FIG. 13 is a block diagram showing the construction of a third embodiment of the image information processing apparatus according to the present invention. The devices 41–47 in FIG. 11 could be replaced by a general purpose electron microscope system. Further, the image processing means 51–57 and their associated frame memories could be replaced by software processes in the computer 101 such as a workstation or the like.

As is apparent from the foregoing, in accordance with the present invention, a defect can be detected without using a golden device or CAD data which are required in the conventional image comparison methods.

In addition, in case of an image having a large pixel value change with a passage of time like a SEM image discussed in the above embodiments, a great amount of noise is detected in the conventional image comparison methods. On the other hand, in the present invention, a defect can be detected without detecting most of the noise.

Moreover, in case of the conventional FFT method, in order to remove a periodic wiring pattern from an image having 512×512 pixels, there are required $1.31 \times 10^8$ additions and subtractions and $8.39 \times 10^8$ multiplications. However, in the present invention, this process can be performed by $5.5 \times 10^5$ additions and subtractions and $1.1 \times 10^6$ multiplications by introducing the Wavelet transform means. In the present invention, any one of all other image processes except the Hough transform requires only a small amount of computations equal to or less than $10^7$. Even in the FFT method, a process such as the Hough transform or the like is required to automatically detect a position and a size of an image. Therefore, the present invention is still advantageous.

The amount of computations of the Hough transform is proportional to the number of pixels of a binarization image to be processed. When the Hough transform for a circle is applied to one pixel having pixel value "1", the amount of computation is proportional to a radius of a circle to be detected. For example, in the case of r=10, $3.6 \times 10^6$ additions/subtractions, $2.4 \times 10^6$ multiplications and $1.2 \times 10^6$ square root extractions are required. Therefore, if the number of pixels to be Hough transformed is small, the amount of computations is less. If the noise removing process and the isolated point removing process as shown in FIGS. 2A and 2B are not performed at all, in case of the image in the above embodiments, approximately 17100 pixels to be Hough transformed each having pixel value "1" are generated. If the noise removing means as shown in FIG. 2A is additionally provided, those pixels are reduced to 3000 pixels and the processing speed is improved to 5.7 times. Further, if the isolated point removing process as shown in FIG. 2B is added, the pixels are reduced to 1200 and the processing speed is improved to more than 14 times. The noise removing means and the isolated point removing means require, in case their processings have a level of $1\times10^6$ operations respectively, only in the order of computations required to perform the Hough transform for 10 pixels. Therefore, the effect of the noise removing means and the isolated point removing means is significant.

As described heretofore, the present invention provides an apparatus for performing a combined process of the Hough transform and the Wavelet transform in a main role with respect to an image having complicated background information such as a semiconductor wafer pattern. By this apparatus, a position and a size of a defect can automatically be detected. The effect of this apparatus is significant in both aspects of defect detection performance and processing speed.

What is claimed is:

1. An image information processing apparatus for inspecting, recognizing or judging an object using its image comprising:

two dimensional Wavelet transform means for applying a two dimensional Wavelet transform to an input digital image;

binarization processing means for applying a threshold value process to longitudinal line detection components and lateral line detection components obtained by the application of the two dimensional Wavelet transform to the input digital image data to create a binarization image of the longitudinal line detection components and a binarization image of the lateral line detection components; and Hough transform means for applying a Hough transform to the binarization images obtained by the binarization processing means to find a position and a size of an object to be detected.

2. The image information processing apparatus according to claim 1, further comprising second binarization processing means for applying a threshold value process to the images in a parameter space obtained by said Hough transform means to detect specific figure information.

3. The image information processing apparatus according to claim 2, further comprising:

labeling processing means for labeling adjacent active images in the binarization images in a parameter space with the same label to group them, the binarization images being obtained by applying a binarization process to the result of the Hough transform process; and center of gravity calculating means for finding center of gravity coordinates for each of the labels obtained by the labeling process.

4. The image information processing apparatus according to claim 1, further comprising noise removing means for applying a localized noise removal operation to the input digital image.

5. The image information processing apparatus according to claim 2, further comprising noise removing means for applying a localized noise removal operation to the input digital image.

6. The image information processing apparatus according to claim 3, further comprising noise removing means for applying a localized noise removal operation to the input digital image.

7. The image information processing apparatus according to claim 4, further comprising isolated point removing means for removing an isolated active image from the binarization images of the longitudinal line detection components and the lateral line detection components obtained by applying the binarization process to the result of the two dimensional Wavelet transform process.

8. The image information processing apparatus according to claim 5, further comprising isolated point removing means for removing an isolated active image from the binarization images of the longitudinal line detection components and the lateral line detection components obtained by applying the binarization process to the result of the two dimensional Wavelet transform process.

9. The image information processing apparatus according to claim 6, further comprising isolated point removing means for removing an isolated active image from the binarization images of the longitudinal line detection components and the lateral line detection components obtained by applying the binarization process to the result of the two dimensional Wavelet transform process.

10. The image information processing apparatus according to claim 1, wherein said binarization processing means for applying a binarization process to the result of the two dimensional Wavelet transform process is an absolute value binarization processing means for applying a threshold value process to the absolute value of the result of the two dimensional Wavelet transform process.

11. The image information processing apparatus according to claim 2, wherein said binarization processing means for applying a binarization process to the result of the two dimensional Wavelet transform process is an absolute value binarization processing means for applying a threshold value process to the absolute value of the result of the two dimensional Wavelet transform process.

12. The image information processing apparatus according to claim 3, wherein said binarization processing means for applying a binarization process to the result of the two dimensional Wavelet transform process is an absolute value binarization processing means for applying a threshold value process to the absolute value of the result of the two dimensional Wavelet transform process.

13. The image information processing apparatus according to claim 1, wherein said Hough transform means is Hough transform means for especially detecting x and y coordinates of a center of a circle and a radius of the circle.

14. The image information processing apparatus according to claim 1, wherein said Hough transform means is means for Hough transforming into the same parameter space the two binarization images respectively corresponding to the longitudinal line detection components and the lateral line detection components obtained by the two dimensional Wavelet transform process.

15. The image information processing apparatus according to claim 1, wherein said Hough transform means is Hough transform means for either one of the two binarization images respectively corresponding to the longitudinal line detection components and the lateral line detection components obtained by the two dimensional Wavelet transform process.

16. The image information processing apparatus according to claim 15, further comprising energy calculating means for calculating energy of each of the longitudinal line detection components and the lateral line detection components obtained by the two dimensional Wavelet transform process; and wherein said Hough transform means Hough transforms to the binarization image corresponding to the components having lower energy.

17. The image information processing apparatus according to claim 13, wherein the binarization threshold value of said second binarization processing means for the parameter space by the Hough transform for a circle is a threshold value changing in accordance with the magnitude of a radius parameter.

18. The image information processing apparatus according to claim 3, further comprising overlap detection removing means for removing, when a plurality of objects to be detected overlap in terms of their positions, the overlapping object or objects.

19. An image information processing method for inspecting, recognizing or judging an object using its image comprising steps that perform the acts of:

applying a two dimensional Wavelet transform to an input digital image;

applying a threshold value process to longitudinal line detection components and lateral line detection components obtained by the application of the two dimensional Wavelet transform to the input digital image data to create a binarization image of the longitudinal line detection components and a binarization image of the lateral line detection components; and applying a Hough transform to the binarization images to find a position and a size of an object to be detected.

20. The image information processing method according to claim 19 that further comprises applying a threshold value process to the images in a parameter space obtained by said Hough transform to detect specific figure information.

21. The image information processing method according to claim 20 that further comprising comprises:

labeling adjacent active images in the binarization images in a parameter space with the same label to group them, the binarization images being obtained by applying a binarization process to the result of the Hough transform process; and finding center of gravity coordinates for each of the labels obtained by the labeling process.

22. The image information processing method according to claim 19, that further comprises applying a localized noise removal operation to the input digital image.

23. The image information processing method according to claim 20 that further comprises applying a localized noise removal operation to the input digital image.

24. The image information processing method according to claim 21 that further comprises applying a localized noise removal operation to the input digital image.

25. The image information processing method according to claim 22 that further comprises removing an isolated active image from the binarization images of the longitudinal line detection components and the lateral line detection components obtained by applying the binarization process to the result of the two dimensional Wavelet transform process.

26. The image information processing method according to claim 23 that further comprises removing an isolated active image from the binarization images of the longitudinal line detection components and the lateral line detection components obtained by applying the binarization process to the result of the two dimensional Wavelet transform process.

27. The image information processing method according to claim 24 that further comprises removing an isolated active image from the binarization images of the longitudinal line detection components and the lateral line detection components obtained by applying the binarization process to the result of the two dimensional Wavelet transform process.

28. The image information processing method according to claim 19, wherein the step that applies said binarization process to the result of the two dimensional Wavelet transform process applies a threshold value process to the absolute value of the result of the two dimensional Wavelet transform process.

29. The image information processing method according to claim 20, wherein the step that applies said binarization process to the result of the two dimensional Wavelet transform process applies a threshold value process to the absolute value of the result of the two dimensional Wavelet transform process.

30. The image information processing method according to claim 21, wherein the step that applies said binarization process to the result of the two dimensional Wavelet transform process applies a threshold value process to the absolute value of the result of the two dimensional Wavelet transform process.

31. The image information processing method according to claim 19, wherein said Hough transform detects x and y coordinates of a center of a circle and a radius of the circle.

32. The image information processing method according to claim 19, wherein said Hough transform transforms into the same parameter space the two binarization images respectively corresponding to the longitudinal line detection components and the lateral line detection components obtained by the two dimensional Wavelet transform process.

33. The image information processing method according to claim 19, wherein said Hough transform is applied to either one of the two binarization images respectively corresponding to the longitudinal line detection components and the lateral line detection components obtained by the two dimensional Wavelet transform process.

34. The image information processing method according to claim 33 that further comprises calculating energy of each of the longitudinal line detection components and the lateral line detection components obtained by the two dimensional Wavelet transform process; and wherein said Hough transform transforms to the binarization image corresponding to the components having lower energy.

35. The image information processing method according to claim 20, wherein said Hough transform detects a radius of a circle and the binarization threshold applied by said threshold value process is changed in accordance with the magnitude of a radius parameter.

36. The image information processing method according to claim 21 that further comprises removing one or more overlapping objects in a plurality of objects to be detected.

* * * * *